United States Patent
Gao et al.

(10) Patent No.: US 12,396,319 B2
(45) Date of Patent: Aug. 19, 2025

(54) ORGANIC LIGHT-EMITTING DEVICE, LIGHT-EMITTING SUBSTRATE AND LIGHT-EMITTING APPARATUS

(71) Applicant: BOE TECHNOLOGY GROUP CO., LTD., Beijing (CN)

(72) Inventors: Rongrong Gao, Beijing (CN); Lei Chen, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 893 days.

(21) Appl. No.: 17/626,147

(22) PCT Filed: Jan. 4, 2021

(86) PCT No.: PCT/CN2021/070101
§ 371 (c)(1),
(2) Date: Jan. 11, 2022

(87) PCT Pub. No.: WO2022/141621
PCT Pub. Date: Jul. 7, 2022

(65) Prior Publication Data
US 2023/0232651 A1     Jul. 20, 2023

(51) Int. Cl.
| | | |
|---|---|---|
| H10K 50/16 | (2023.01) | |
| H10K 50/15 | (2023.01) | |
| H10K 50/18 | (2023.01) | |
| H10K 85/40 | (2023.01) | |
| H10K 85/60 | (2023.01) | |
| H10K 101/30 | (2023.01) | |

(52) U.S. Cl.
CPC ........... H10K 50/166 (2023.02); H10K 50/15 (2023.02); H10K 50/18 (2023.02); H10K 50/181 (2023.02); H10K 85/40 (2023.02); H10K 85/654 (2023.02); H10K 85/6572 (2023.02); H10K 85/6574 (2023.02); H10K 85/6576 (2023.02); H10K 85/658 (2023.02); H10K 2101/30 (2023.02)

(58) Field of Classification Search
None
See application file for complete search history.

(56) References Cited

U.S. PATENT DOCUMENTS

| | | | | |
|---|---|---|---|---|
| 2006/0042685 | A1* | 3/2006 | Wang | H10K 50/125 |
| | | | | 136/252 |
| 2006/0083946 | A1 | 4/2006 | Lee et al. | |
| 2008/0103315 | A1* | 5/2008 | Egawa | H10K 85/6572 |
| | | | | 313/504 |
| 2009/0243473 | A1* | 10/2009 | Iwakuma | H10K 50/14 |
| | | | | 313/504 |
| 2010/0314648 | A1* | 12/2010 | Fehrer | H10K 50/131 |
| | | | | 257/98 |
| 2016/0359128 | A1* | 12/2016 | Tsukamoto | H10K 50/15 |
| 2017/0194591 | A1* | 7/2017 | Wang | H10K 50/18 |
| 2017/0213875 | A1* | 7/2017 | Bi | H10K 50/19 |
| 2019/0051834 | A1 | 2/2019 | Liu et al. | |
| 2019/0067589 | A1* | 2/2019 | Yoon | H10K 50/11 |
| 2019/0386234 | A1 | 12/2019 | Cheng et al. | |
| 2020/0067007 | A1 | 2/2020 | Mou et al. | |
| 2021/0305516 | A1 | 9/2021 | Heo et al. | |
| 2022/0093873 | A1 | 3/2022 | Kim et al. | |

FOREIGN PATENT DOCUMENTS

| | | |
|---|---|---|
| CN | 103922995 | 7/2014 |
| CN | 110734396 | 1/2020 |
| CN | 111969119 | 11/2020 |
| WO | WO 2019/174650 | 9/2019 |
| WO | WO 2020/022771 | 1/2020 |

OTHER PUBLICATIONS

Kumar, Manish, and Luiz Pereira. "Effect of the Host on Deep-Blue Organic Light-Emitting Diodes Based on a TADF Emitter for Roll-Off Suppressing." Nanomaterials 9.9 (2019): 1307. (Year: 2019).*
Chasse, T., et al. "Band alignment at organic-inorganic semiconductor interfaces: α-NPD and CuPc on InP (110)." Journal of applied physics 85.9 (1999): 6589-6592. (Year: 1999).*
Lee, Seokjae, et al. "Effect of triplet multiple quantum well structures on the performance of blue phosphorescent organic light-emitting diodes." Nanoscale research letters 7 (2012): 1-5. (Year: 2012).*
Gong, Myoung-Seon, Jae-Ryung Cha, and Chil Won Lee. "Synthesis and device properties of mCP analogues based on fused-ring carbazole moiety." Organic Electronics 42 (2017): 66-74. (Year: 2017).*
Technical data sheet for 3,3'-di(9H-carbazol-9-yl)-1,1'-biphenyl (mCBP) by Ossila, no date given, 7 pages. (Year: None).*
PCT International Search Report and Written Opinion for corresponding Application No. PCT/CN2021/070101, 9 pages.

* cited by examiner

*Primary Examiner* — Robert S Loewe
(74) *Attorney, Agent, or Firm* — Dority & Manning, P.A.

(57) ABSTRACT

An organic light-emitting device includes: an anode, an emitting layer, and a cathode that are stacked; a first functional material layer located between the emitting layer and the anode; and a second functional material layer located between the emitting layer and the cathode. Under a same test condition, a hole mobility of a material of the first functional material layer is at least ten times an electron mobility of a material of the second functional material layer.

20 Claims, 2 Drawing Sheets

ORGANIC LIGHT-EMITTING DEVICE, LIGHT-EMITTING SUBSTRATE AND LIGHT-EMITTING APPARATUS

CROSS-REFERENCE TO RELATED APPLICATION

This application is a national phase entry under 35 USC 371 of International Patent Application No. PCT/CN2021/070101, filed on Jan. 4, 2021, which is incorporated herein by reference in its entirety.

TECHNICAL FIELD

The present disclosure relates to the field of illumination and display technologies, and in particular, to an organic light-emitting device, a light-emitting substrate and a light-emitting apparatus.

BACKGROUND

Organic light-emitting diodes (OLEDs), which have been hailed as a next-generation "star" display technology, have characteristics of self-luminescence, wide visual angles, fast response time, high luminous efficiencies, low operating voltages, small substrate thicknesses, capabilities of being used to manufacture large-size flexible substrates, simple manufacturing processes and the like.

SUMMARY

In an aspect, an organic light-emitting device is provided, The organic light-emitting device includes: an anode, an emitting layer, and a cathode that are stacked; a first functional material layer located between the emitting layer and the anode; and a second functional material layer located between the emitting layer and the cathode. Under a same test condition, a hole mobility of a material of the first functional material layer is at least ten times an electron mobility of a material of the second functional material layer.

In some embodiments, the second functional material layer includes an electron transport layer and a hole blocking layer. An electron mobility of a material of the electron transport layer is the same as an electron mobility of a material of the hole blocking layer; or under a same test condition, the electron mobility of the material of the hole blocking layer is less than the electron mobility of the material of the electron transport layer.

In some embodiments, a lowest triplet energy of the material of the electron transport layer is greater than a lowest triplet energy of the material of the hole blocking layer.

In some embodiments, the material of the electron transport layer and the material of the hole blocking layer are each independently selected from compounds containing at least one heteroaryl which contains at least two N atoms.

In some embodiments, the material of the electron transport layer is a compound based on a spirocyclic aromatic hydrocarbon structure.

In some embodiments, the material of the electron transport layer is selected from any one or a combination of two or more of structures shown in a general formula (I).

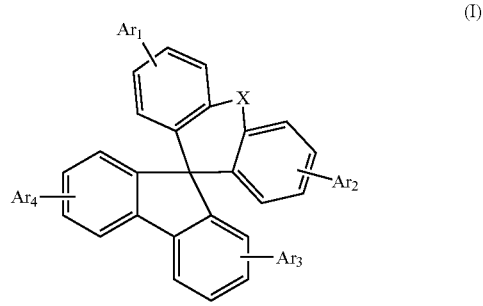

In the general formula (I), X is selected from any of $C(R)_2$, O, S, N(R), and a single bond, $Ar_1$ to $Ar_4$ are able to exist simultaneously or separately, and are each independently selected from aryl or heteroaryl with 5 to 30 ring atoms substituted or unsubstituted by a substituent $R_1$, at least one of $Ar_1$ to $Ar_4$ is selected from any of structures as shown in a following general formula (II), and the substituent $R_1$ is selected from any of tert-butyl, cyano, aryl or heteroaryl with 5 to 30 ring atoms, and $—Y_1(Ar)_n$.

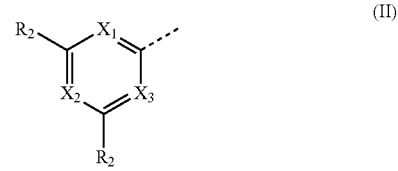

In the general formula (II), $X_1$, $X_2$, and $X_3$ are each independently selected from any of $C(R_2)$ and N, and at least two of $X_1$, $X_2$, and $X_3$ are selected from N.

Each $R_2$ is the same or different, and is independently selected from any of H and aryl or heteroaryl with 5 to 30 ring atoms. In a case where $R_2$ is selected from the aryl or heteroaryl with 5 to 30 ring atoms, the aryl or heteroaryl has or has no the substituent R1.

$Y_1$ is selected from any of carbon, nitrogen, phosphorus, silicon, boron, $C(R_3)_2$, $Si(R_3)_2$, $C(=O)$, $C(=NR)$, $C(=C(R)_2)$, $S(=O)$, $S(=O)_2$, and $P(=O)$, and n is an integer greater than or equal to 1. Each Ar is the same or different, and is independently selected from aryl or heteroaryl, or in a case where n is an integer greater than or equal to 2, at least two Ars are connected into a ring through the single bond or a first bridging group. The first bridging group is selected from $B(R)$, $C(R)_2$, $Si(R)_2$, $C(=O)$, $C(=NR)$, $C(=C(R)_2)$, O, S, $S(=O)$, $S(=O)_2$, $N(R)$, $P(R)$, and $P(=O)(R)$, $R_3$ is selected from any of H and methyl, and R is selected from any of H, methyl, aryl or heteroaryl.

In some embodiments, the material of the electron transport layer is selected from any one or a combination of two or more of following compounds:
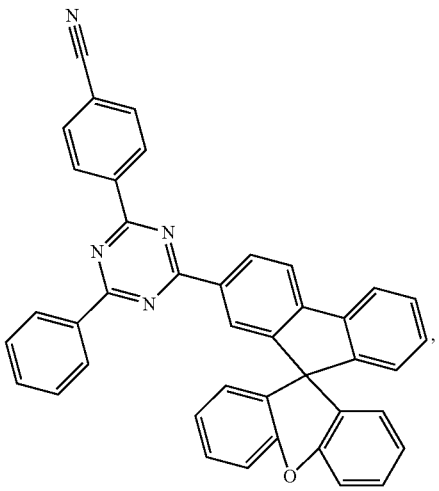
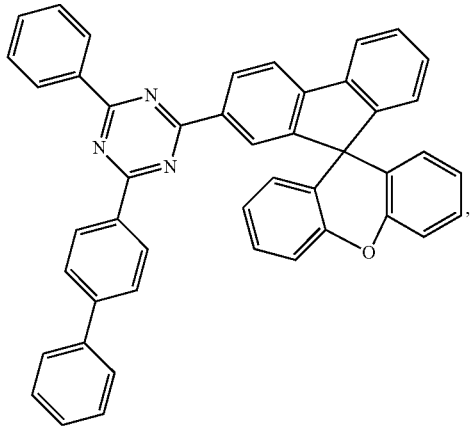
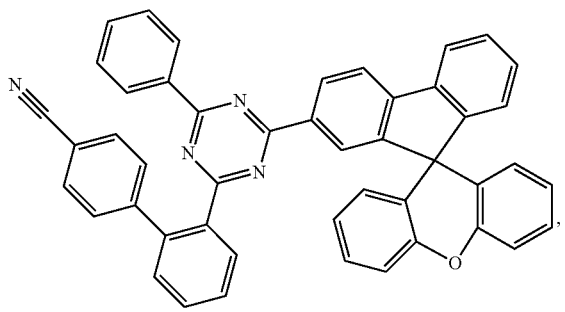
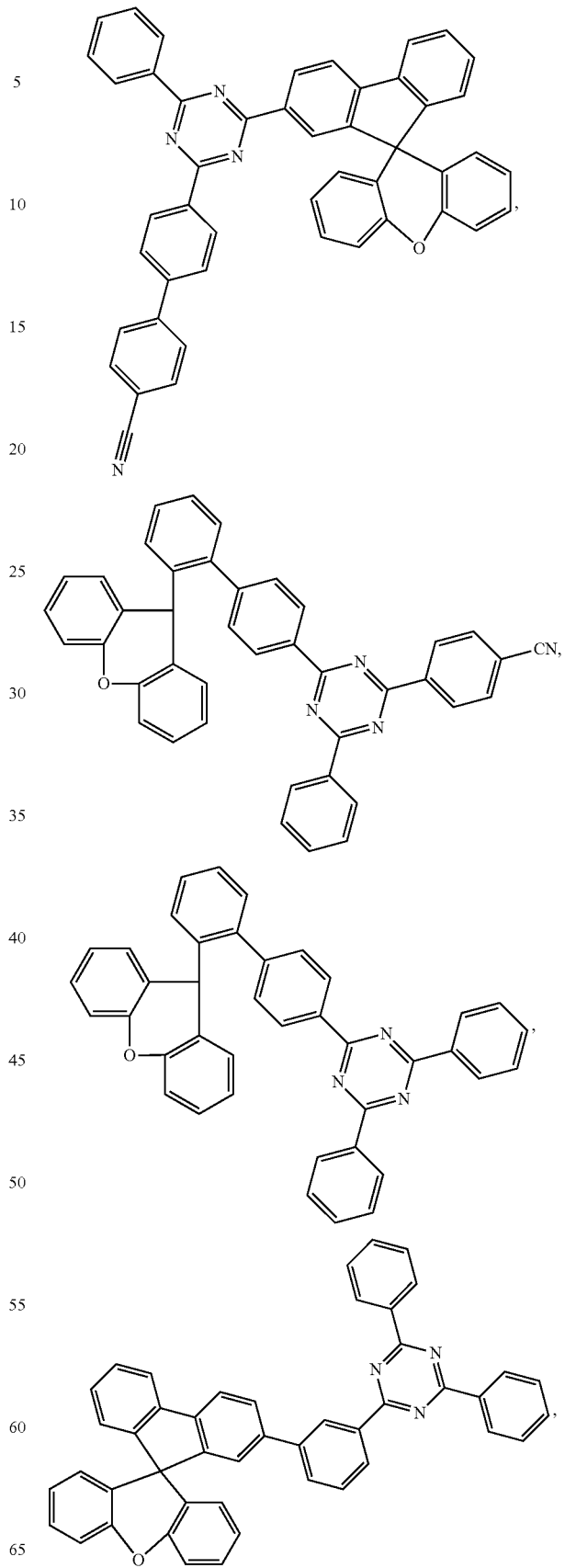

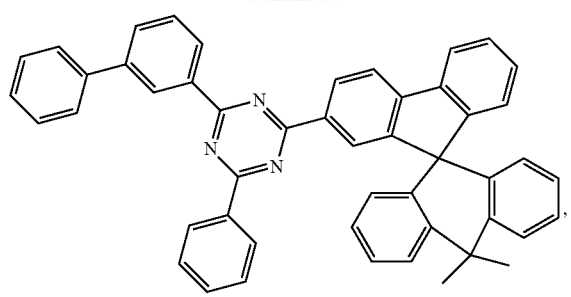
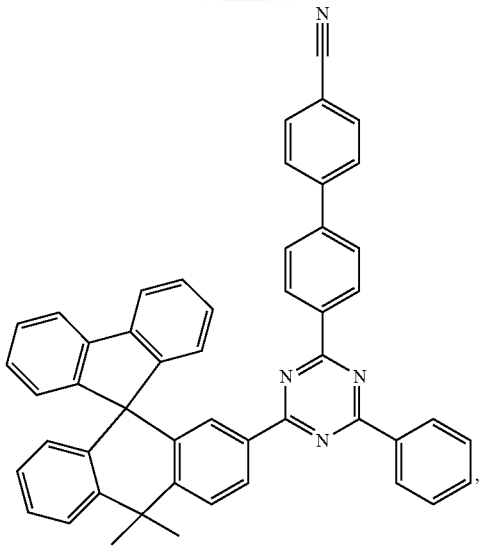
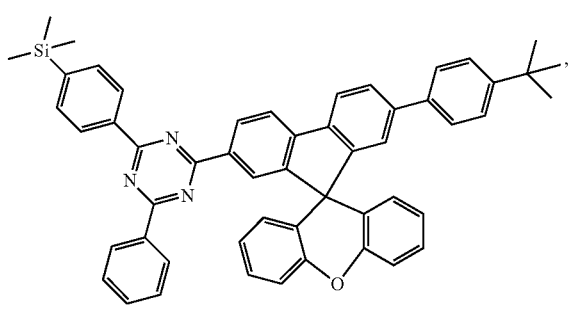
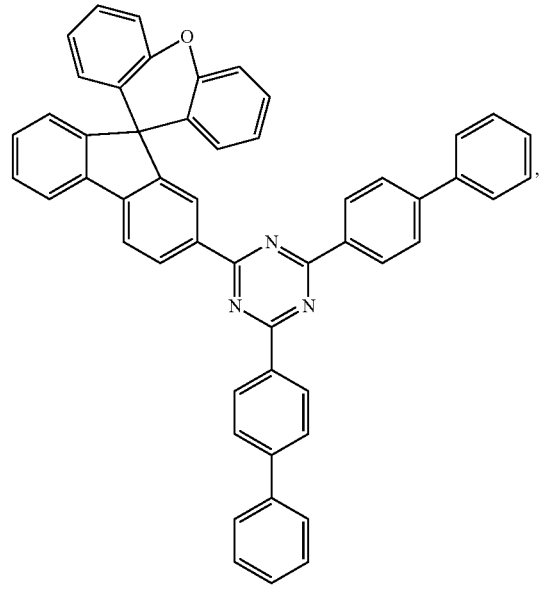
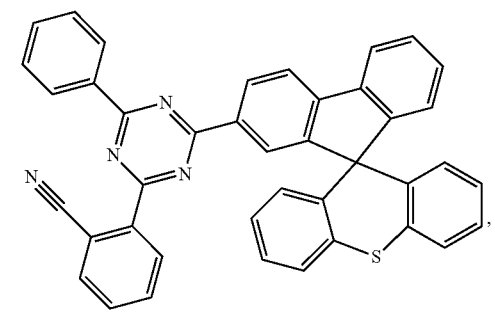
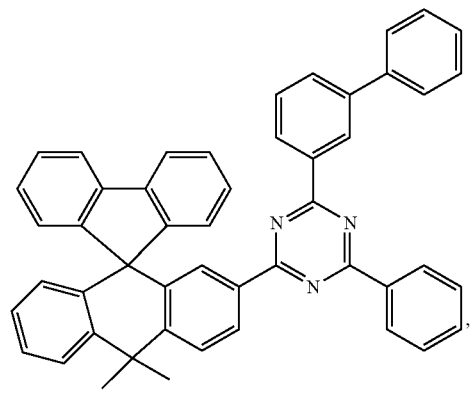
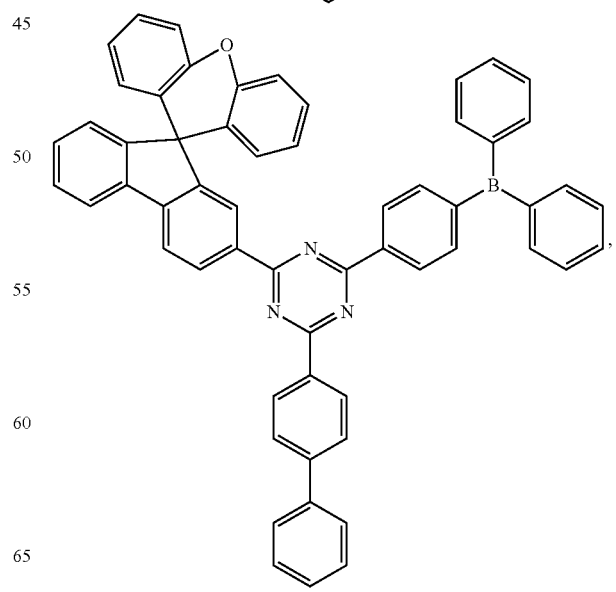

-continued

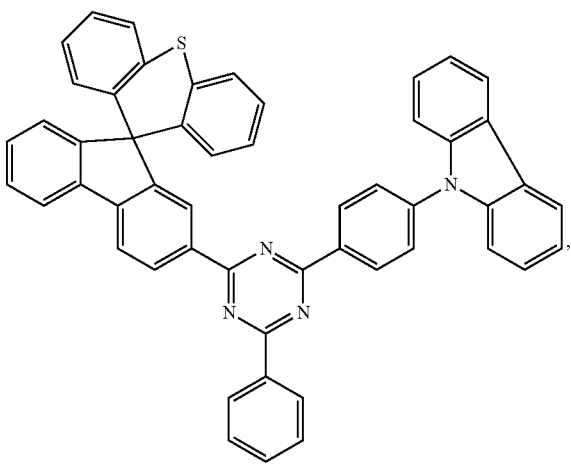

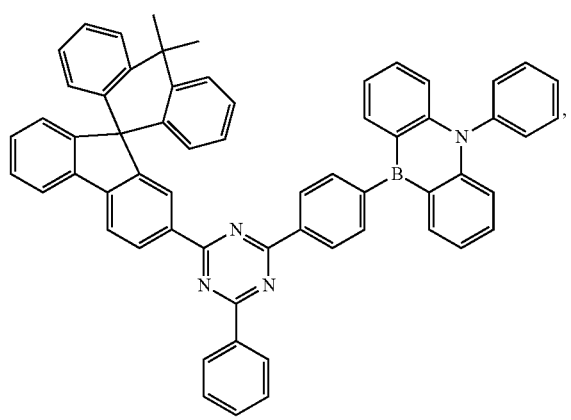

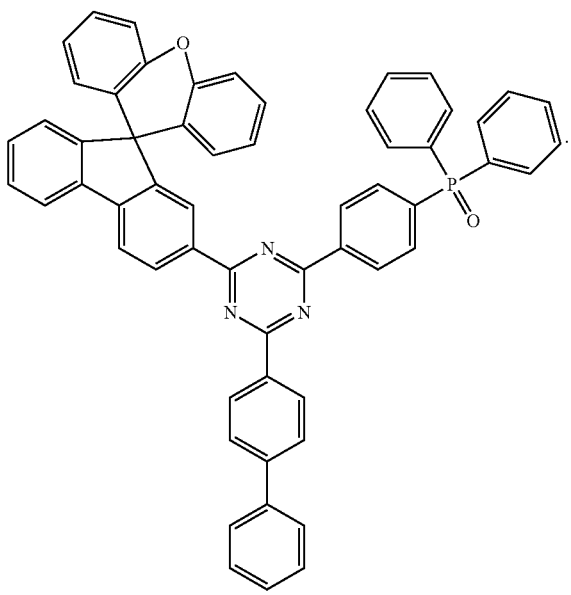

In some embodiments, the material of the hole blocking layer is selected from any one or a combination of two or more of structures as shown in a general formula (III).

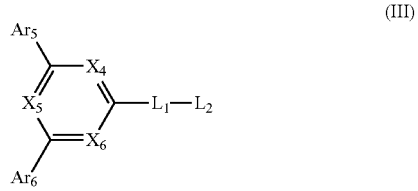

(III)

In the general formula (III), $X_4$, $X_5$, and $X_6$ are each independently selected from any of C(R) and N, and at least two of $X_4$, $X_5$, and $X_6$ are selected from N; and $Ar_5$, $Ar_6$, and $L_2$ are each independently selected from aryl with 6 to 60 carbon atoms substituted or unsubstituted by the substituent $R_1$, or heteroaryl with 2 to 60 carbon atoms substituted or unsubstituted by the substituent R1.

$L_1$ is selected from the single bond, divalent aryl with 6 to 60 carbon atoms substituted or unsubstituted by the substituent $R_1$, or divalent heteroaryl with 2 to 60 carbon atoms substituted or unsubstituted by the substituent $R_1$.

$R_1$ is independently selected from any of tent-butyl, cyano, aryl or heteroaryl with 5 to 30 ring atoms, and $-Y_1(Ar)_n$, $Y_1$ is selected from carbon, nitrogen, phosphorus, silicon, boron, $C(R_3)_2$, $Si(R_3)_2$, $C(=O)$, $C(=NR)$, $C(=C(R)_2)$, $S(=O)$, $S(=O)_2$, and $P(=O)$, and n is an integer greater than or equal to 1. Each Ar is the same or different, and is independently selected from aryl or heteroaryl, or Ar and the aryl or heteroaryl substituted by the substituent $R_1$ are connected as a ring through a single bond or a second bridging group, and/or at least two Ars, in a case where n is an integer greater than or equal to 2, are connected into a ring through the single bond or a second bridging group, and each second bridging group is selected from B(R), $C(R)_2$, $Si(R)_2$, $O(=O)$, $C(=NR)$, $C(=C(R)_2)$, O, S, $S(=O)$, $S(=O)_2$, N(R), P(R), and $P(=O)(R)$.

$R_3$ is selected from any of H and methyl, and R is selected from any of H, methyl, aryl and heteroaryl.

In some embodiments, in the general formula (III), in a case where $L_1$ is selected from bivalent bicyclic aryl substituted or unsubstituted by the substituent $R_1$, at least one single ring in the divalent bicyclic aryl has a group attached at a meta position and/or an ortho position; and in a case where $L_1$ is selected from monocyclic aryl substituted or unsubstituted by the substituent $R_1$, $L_2$ and azine are attached at a meta position or an ortho position of $L_1$.

In some embodiments, the material of the hole blocking layer is selected from any one or a combination of two or more of following structures:

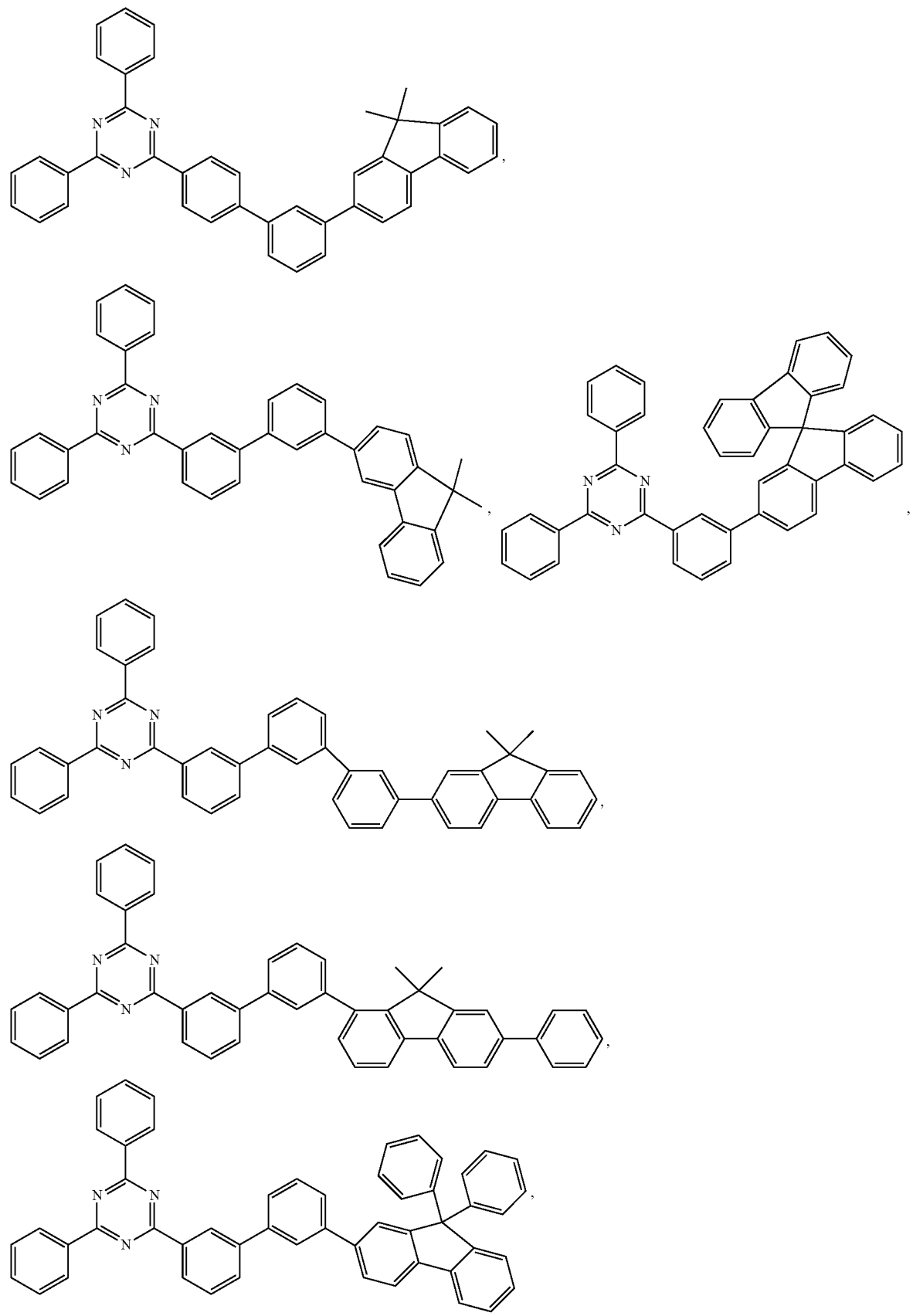

-continued

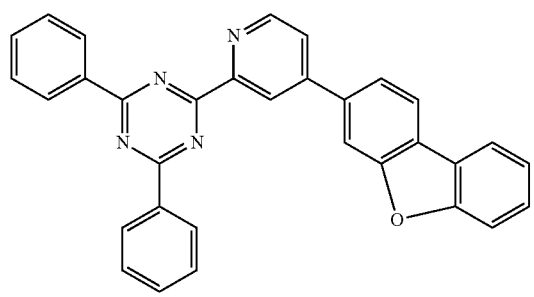

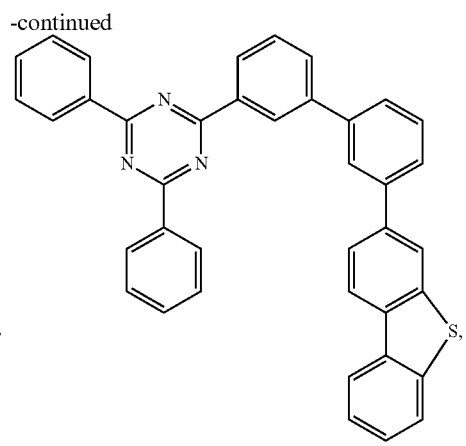

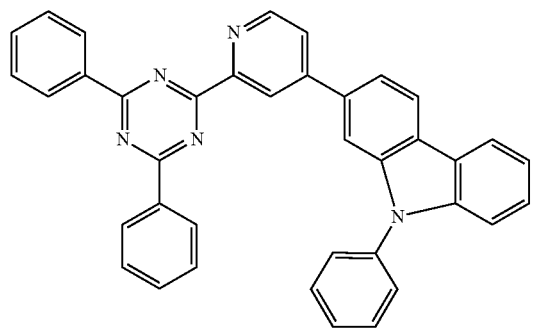

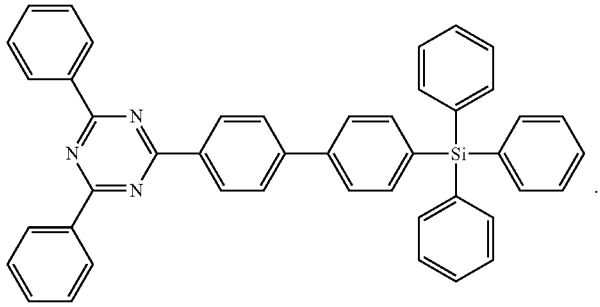

In some embodiments, the first functional material layer includes a hole transport layer and an electron blocking layer. A hole mobility of a material of the hole transport layer is the same as a hole mobility of a material of the electron blocking layer; or under a same test condition, the hole mobility of the material of the electron blocking layer is not less than one tenth of the hole mobility of the material of the hole transport layer.

In some embodiments, a difference between a HOMO energy level of the material of the hole transport layer and a HOMO energy level of the material of the electron blocking layer is greater than or equal to −0.5 eV, and is less than or equal to 0.3 eV.

In some embodiments, a lowest triplet energy of the hole transport layer is greater than a lowest triplet energy of the electron blocking layer.

In some embodiments, a material of the emitting layer includes a host material, A difference between a highest occupied molecular orbital (HOMO) energy level of the material of the hole blocking layer and a HOMO energy level of the host material is greater than or equal to 0.1 eV.

In some embodiments, a lowest triplet energy of the hole blocking layer is greater than a lowest triplet energy of the host material.

In some embodiments, the first functional material layer includes an electron blocking layer. A difference between the HOMO energy level of the host material and a HOMO energy level of the electron blocking layer is less than or equal to 0.3 eV.

In some embodiments, a lowest triplet energy of the electron blocking layer is greater than the lowest triplet energy of the host material.

In some embodiments, the material of the hole transport layer and the material of the electron blocking layer are each independently selected from any of aromatic amine compounds.

In another aspect, a light-emitting substrate is provided, including: a base and a plurality of light-emitting devices disposed on the base. At least one light-emitting device is selected from the organic light-emitting device as described above.

In yet another aspect, a light-emitting apparatus is provided, including the light-emitting substrate as described above.

BRIEF DESCRIPTION OF THE DRAWINGS

In order to describe technical solutions in the present disclosure more clearly, accompanying drawings to be used in some embodiments of the present disclosure will be introduced briefly below. However, the accompanying drawings to be described below are merely accompanying drawings of some embodiments of the present disclosure, and a person of ordinary skill in the art may obtain other drawings according to these drawings. In addition, the accompanying drawings to be described below may be regarded as schematic diagrams, and are not limitations on actual sizes of products, actual processes of methods and actual timings of signals involved in the embodiments of the present disclosure.

DETAILED DESCRIPTION

Figure 1:
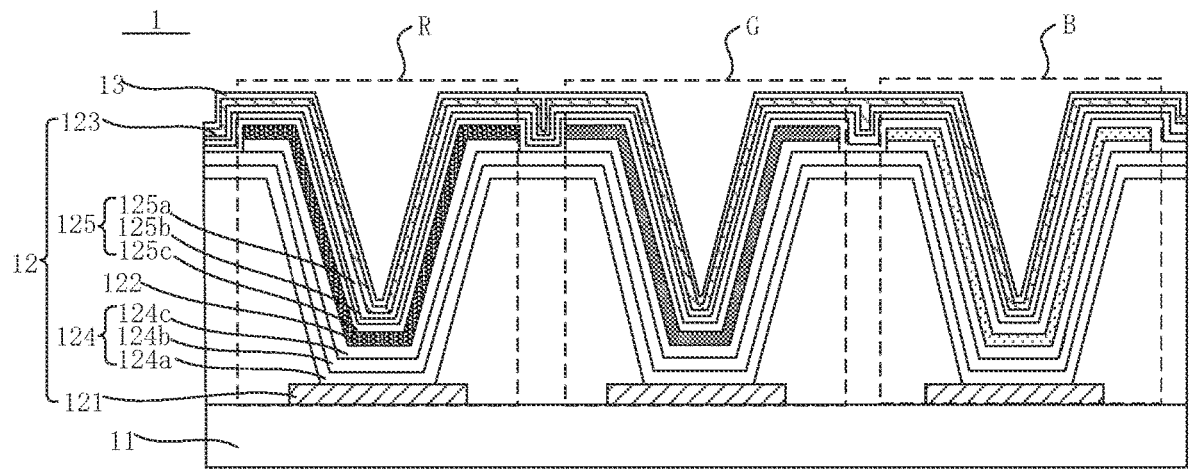
FIG. 1 is a sectional structural view of a light-emitting substrate, in accordance with some embodiments.

Technical solutions in some embodiments of the present disclosure will be described clearly and completely below with reference to the accompanying drawings. However, the described embodiments are merely some but not all embodiments of the present disclosure. All other embodiments obtained based on the embodiments of the present disclosure by a person of ordinary skill in the art shall be included in the protection scope of the present disclosure.

Unless the context requires otherwise, throughout the description and the claims, the term "comprise" and other forms thereof such as the third-person singular form "comprises" and the present participle form "comprising" are construed as an open and inclusive meaning, i.e., "including, but not limited to". In the description of the specification, the terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials, or characteristics may be included in any one or more embodiments or examples in any suitable manner.

Hereinafter, the terms "first" and "second" are used for descriptive purposes only, and are not to be construed as indicating or implying relative importance or implicitly indicating the number of indicated technical features. Thus, a feature defined with "first" or "second" may explicitly or implicitly include one or more of the features. In the description of the embodiments of the present disclosure, the term "a plurality of", "the plurality of" or "multiple" means two or more unless otherwise specified.

The phrase "at least one of A, B and C" has a same meaning as the phrase "at least one of A, B or C", and they both include the following combinations of A, B and C: only A, only B, only C, a combination of A and B, a combination of A and C, a combination of B and C, and a combination of A, B and C.

The phrase "A and/or B" includes the following three combinations: only A, only B, and a combination of A and B.

The phrase "applicable to" or "configured to" used herein has an open and inclusive meaning, which does not exclude devices that are applicable to or configured to perform additional tasks or steps.

In addition, the phrase "based on" used herein is meant to be open and inclusive, since a process, step, calculation or other action that is "based on" one or more of the stated conditions or values may, in practice, be based on additional conditions or values exceeding those stated.

Exemplary embodiments are described herein with reference to sectional views and/or plan views as idealized exemplary drawings. In the drawings, thicknesses of layers and regions are enlarged for clarity. Thus, variations in shapes relative to the accompanying drawings due to, for example, manufacturing technologies and/or tolerances may be envisaged. Therefore, the exemplary embodiments should not be construed as being limited to the shapes of the regions shown herein, but including shape deviations due to, for example, manufacturing. For example, an etched region shown to have a rectangular shape generally has a feature of being curved. Therefore, the regions shown in the accompanying drawings are schematic in nature, and their shapes are not intended to show actual shapes of the regions in a device, and are not intended to limit the scope of the exemplary embodiments.

Some embodiments of the present disclosure provide a light-emitting apparatus which includes a light-emitting substrate. Of course, the light-emitting apparatus may further include other components. For example, it may include a circuit for providing electrical signals to the light-emitting substrate, so as to drive the light-emitting substrate to emit light. The circuit may be referred to as a control circuit, and may include a circuit board electrically connected to the light-emitting substrate and/or an integrated circuit (IC) electrically connected to the light-emitting substrate.

In some embodiments, the light-emitting apparatus may be an illumination apparatus. In this case, the light-emitting substrate may be an illumination substrate. For example, the light-emitting substrate may be used as a light source to achieve an illumination function. For example, the light-emitting substrate may be a backlight module in a liquid crystal display apparatus, a lamp for internal or external illumination, or a signal lamp.

In some other embodiments, the light-emitting apparatus may be a display apparatus. In this case, the light-emitting substrate is a display substrate, and is used to achieve a function of displaying images (i.e., pictures). The light-emitting apparatus may include a display or a product including the display. The display may be a flat panel display (FPD), a micro display, etc. If classified according to whether users can see a scene behind the display, the display may be a transparent display or an opaque display. If classified according to whether the display can be bent or curled, the display may be a flexible display or a common display (which may be referred to as a rigid display). For example, the product including the display may include a computer display, a television, a billboard, a laser printer with a display function, a telephone, a mobile phone, a personal digital assistant (PDA), a laptop computer, a digital camera, a portable camcorder, a viewfinder, a vehicle, a large-area wall, a screen in a theater, or a sign in a stadium.

In some embodiments, as shown in FIG. 1, the light-emitting substrate 1 may include a base 11 and a plurality of organic light-emitting devices 12 disposed on the base 11. The base 11 may be a flexible base or a rigid base. In a case where the base 11 is the flexible base, the base 11 may be made of polyimide (PI). In a case where the base 11 is the rigid base, the base 11 may be made of glass. Herein, the base 11 may be a base on which pixel driver circuits have been formed.

The light-emitting substrate 1 may be a top-emission light-emitting substrate (light emitted by the organic light-emitting device 12 is emitted from a side thereof away from the base 11), a bottom-emission light-emitting substrate (the light emitted by the organic light-emitting device 12 is emitted from a side of the base 11), or a double-sided emission light-emitting substrate.

For example, as shown in FIG. 1, in an example in which the light-emitting substrate 1 is the top-emission light-emitting substrate, the light-emitting substrate 1 may further include a light extraction layer 13 disposed on a side of the organic light-emitting devices 12 away from the base 11. The light extraction layer 13 is configured to extract light emitted by each organic light-emitting device 12.

In some embodiments, at least one organic light-emitting device 12 may include an anode 121, an emitting layer (EML) 122, and a cathode 123 that are stacked, a first functional material layer 124 located between the emitting layer 122 and the anode 121, and a second functional material layer 125 located between the emitting layer 122 and the cathode 123.

The first functional material layer 124 may include a hole inject layer (HIL) 124a and a hole transport layer (HTL) 124b, and may further include an electron blocking layer (EBL) 124c, which is not specifically limited herein, as long as the first functional material layer 124 can realize injection and transport of holes. The second functional material layer 125 may include an electron inject layer (EIL) 125a and an electron transport layer (ETL) 125b, and may further include a hole blocking layer (HBL) 125c, which is not specifically limited herein, as long as the second functional material layer 125 can realize injection and transport of electrons.

According to structures and functions of the first functional material layer 124 and the second functional material layer 125, it will be seen that a light-emitting principle of the organic light-emitting device 12 is that: when a voltage is applied across the anode 121 and the cathode 123, electrons are injected through the electron inject layer 125a, and are transported to the emitting layer 122 through the electron transport layer 125b and the hole blocking layer 125c; holes are injected through the hole inject layer 124a, and are transported to the emitting layer 122 through the hole transport layer 124b and the electron blocking layer 124c; and the electrons and the holes recombine in the emitting layer 122 to generate singlet excitons and triplet excitons, and light is emitted through de-excitation and radiation of excitons.

In this process, characteristics of materials of the functional material layers and a matching degree of mobilities and a matching degree of energy levels between the functional material layers will affect injection and transport of carriers inside the organic light-emitting device 12, a formation and quenching of excitons and other characteristics, thus affecting a light-emitting characteristic of the organic light-emitting device 12.

A mobility refers to an average drift velocity of carriers (the electrons and the holes) under the influence of a unit electric field, i.e., a magnitude of a velocity of movement of carriers under action of an electric field. The faster the carriers move, the greater the mobility will be; and the slower the carriers move, the smaller the mobility will be.

The mobility is related to the characteristics of the material, but has little relation to the number and thicknesses of layers in the first functional material layer 124 and the second functional material layer 125. It can be seen from the above that in the embodiments provided in the present disclosure, descriptions are made by taking examples in which the first functional material layer 124 includes the hole inject layer 124a, the hole transport layer 124b, and the electron blocking layer 124c, and the second functional material layer 125 includes the electron inject layer 125a, the electron transport layer 125b, and the hole blocking layer 125c, and those skilled in the art can understand that the following descriptions of materials of the first functional material layer 124 and the second functional material layer 125 are also applicable to a case where the first functional material layer 124 only includes the hole inject layer 124a and the hole transport layer 124b, and/or the second functional material layer 125 only includes the electron inject layer 125a and the electron transport layer 125b. The number of layers and a thickness of each layer of the first functional material layer 124 and the second functional material layer 125 is not limited.

Driver circuits connected to the organic light-emitting devices may further be provided in the light-emitting substrate 1. The driver circuits may be connected to the control circuit, so as to drive, according to electrical signals input by the control circuit, the organic light-emitting devices to emit light. The driver circuit may be an active driver circuit or a passive driver circuit.

The light-emitting substrate 1 may emit monochromatic light (i.e., light of a single color) or color-adjustable light.

In a first example, the light-emitting substrate 1 may emit the monochromatic light. In this example, the plurality of organic light-emitting devices (e.g., all organic light-emitting devices) included in the light-emitting substrate 1 all emit the monochromatic light (e.g., red light). The light-emitting substrate 1 may be used for illumination. That is, the light-emitting substrate 1 may be applied to the illumination apparatus. The light-emitting substrate 1 may also be used to display a single-color image or picture. That is, the light-emitting substrate 1 may be applied to the display apparatus.

In a second example, the light-emitting substrate 1 may emit the color-adjustable light (i.e., colored light). In this example, the plurality of organic light-emitting devices included in the light-emitting substrate 1 emit light of different colors. By controlling a brightness of each organic light-emitting device, a color and a brightness of mixed light emitted by the light-emitting substrate 1 may be controlled, and colored light may be emitted.

In this example, the light-emitting substrate may be used to display images or pictures. That is, the light-emitting substrate may be applied to the display apparatus. Of course, the light-emitting substrate may also be used in the illumination apparatus.

Herein, as shown in FIG. 1, in an example in which at least three organic light-emitting devices 12 in the light-emitting substrate each include an anode 121, an emitting layer 122, and a cathode 123 that are stacked, a first functional material layer 124 located between the emitting layer 122 and the anode 121, and a second functional material layer 125 located between the emitting layer 122 and the cathode 123, the at least three organic light-emitting devices may include a light-emitting device R that emits red light, a light-emitting device G that emits green light, and a light-emitting device B that emits blue light.

In some embodiments, a material of the emitting layer 122 may include a host material and a dopant material.

According to a different color of light emitted by an emitting layer 122, the emitting layer 122 may include a different host material and a different dopant material.

In some embodiments, under a same test condition, a hole mobility of a host material of the emitting layer 122 in the light-emitting device R that emits red light is substantially the same as a hole mobility of a host material of the emitting layer 122 in the light-emitting device G that emits green light, and an electron mobility of the host material of the emitting layer 122 in the light-emitting device R that emits red light is slightly greater than an electron mobility of the host material of the emitting layer 122 in the light-emitting device G that emits green light. A hole mobility of a host material of the emitting layer 122 in the light-emitting device B that emits blue light is less than the hole mobility of the host material of the emitting layer 122 in the light-emitting device R that emits red light, and an electron mobility of the host material of the emitting layer 122 in the light-emitting device B that emits blue light is comparable to the electron mobility of the host material of the emitting layer 122 in the light-emitting device G that emits green light.

That is, transport velocities of carriers in the emitting layer 122 of the light-emitting device R that emits red light and corresponding transport velocities of carriers in the emitting layer 122 of the light-emitting device G that emits green light are basically the same, and a transport of carriers in the host material of the emitting layer 122 in the light-emitting device B that emits blue light is not balanced, in which a serious problem of a hole transport delay exists.

For example, in a case where the organic light-emitting device 12 is the light-emitting device R that emits red light, the host material of the emitting layer 122 may be a dual-host material. That is, the host material of the emitting layer 122 includes both a compound with a function of transporting electrons and a single-host material with a function of transporting holes. In this case, the emitting layer 122 may be formed by evaporating the dual-host material. Of course, the host material of the emitting layer 122 may also be a single compound with functions of transporting electrons and holes.

Herein, a space-charge-limited-current (SCLC) method may be adopted to test the electron mobility and the hole mobility of the host material of the emitting layer. In some embodiments, under a test condition of an electric field intensity of 5000 $V^{1/2}/m^{1/2}$, in the light-emitting device R that emits red light, the electron mobility of the host material of the emitting layer may be any value from $10^{-7}$ $cm^2V^{-1}s^{-1}$ to $10^{-6}$ $cm^2V^{-1}s^{-1}$, inclusive, and the hole mobility of the host material of the emitting layer may be any value from $10^{-7}$ $cm^2V^{-1}s^{-1}$ to $10^{-6}$ $cm^2V^{-1}s^{-1}$, inclusive.

In a case where the organic light-emitting device 12 is the light-emitting device G that emits green light, the host material of the emitting layer 122 may also be a dual-host material, or the single compound with functions of transporting electrons and holes. In this case, under a same test condition, the electron mobility and the hole mobility of the host material of the emitting layer 122 are also substantially the same.

Herein, the electron mobility and the hole mobility of the host material of the emitting layer may also be tested adopting the SCLC method. In some embodiments, under the test condition of the electric field intensity of 5000 $V^{1/2}/m^{1/2}$, in the light-emitting device G that emits green light, the electron mobility of the host material of the emitting layer may be any value from $10^{-8}$ $cm^2V^{-1}s^{-1}$ to $10^{-7}$ $cm^2V^{-1}s^{-1}$, inclusive; and the hole mobility of the host material of the emitting layer may be any value from $10^{-7}$ $cm^2V^{-1}s^{-1}$ to $10^{-6}$ $cm^2V^{-1}s^{-1}$, inclusive.

In a case where the organic light-emitting device 12 is the light-emitting device B that emits blue light, the host material of the emitting layer 122 is a single-host material. In this case, under the same test condition, the electron mobility of the host material of the emitting layer 122 is greater than the hole mobility of the host material of the emitting layer 122.

Herein, the electron mobility and the hole mobility of the host material of the emitting layer 122 may also be tested adopting the SCLC method. In some embodiments, under the test condition of the electric field intensity of 5000 $V^{1/2}/m^{1/2}$, in the light-emitting device B that emits blue light, the electron mobility of the host material of the emitting layer 122 is any value from $10^{-7}$ $cm^2V^{-1}s^{-1}$ to $10^{-8}$ $cm^2V^{-1}s^{-1}$, inclusive; and the hole mobility of the host material of the emitting layer 122 is any value from $10^{-8}$ $cm^2V^{-1}s^{-1}$ to $10^{-9}$ $cm^2V^{-1}s^{-1}$, inclusive.

Figure 2:
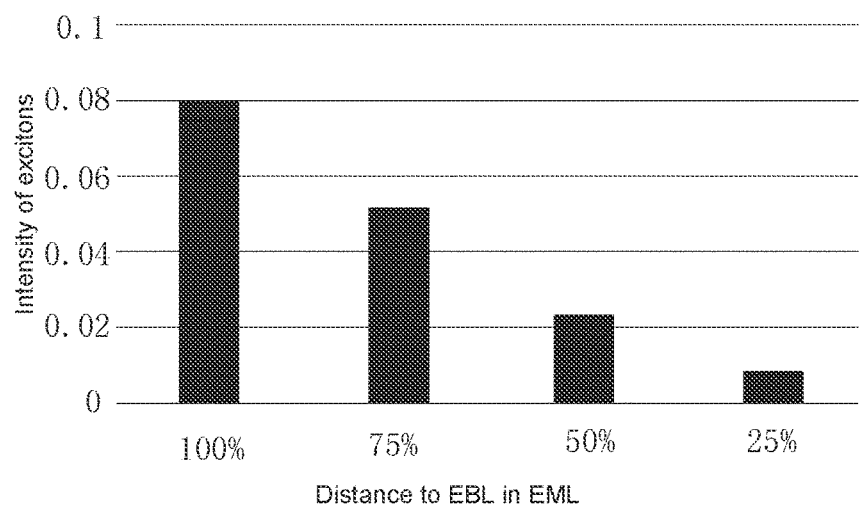
FIG. 2 is a distribution diagram of recombination zones of excitons in an emitting layer, in accordance with some embodiments.

Based on this, researches on recombination zones of excitons of currently existing organic light-emitting devices (e.g., the light-emitting device that emits blue light) show that in the material selection of currently existing functional material layers, a distribution diagram of recombination zones of the excitons in the emitting layer 122 is as shown in FIG. 2. It will be seen from FIG. 2 that the closer to the electron blocking layer 124c, the greater an intensity of the excitons, which indicates that the recombination zone of most of the excitons is at an interface between the electron blocking layer 124c and the emitting layer 122.

Herein, the intensity of excitons, different from a concentration of excitons, is a measure of a luminous intensity of excitons when the excitons are deexcited. The intensity of excitons is not only related to the concentration of excitons, but also related to other factors such as lifetimes of excitons. However, in a case where other influencing factors are certain, the concentration of excitons is a main factor that affects the intensity of excitons. Therefore, in an entire device, the intensity of excitons and the concentration of excitons have a same or similar changing trend. Based on this, according to a case where the intensity of the excitons gradually decreases as the emitting layer is farther away from the electron blocking layer 124c as shown in FIG. 2, it will be seen that the concentration of the excitons also gradually decreases as the emitting layer is farther away from the electron blocking layer 124c. That is, in a case where the number of excitons is certain, the recombination zone of most of the excitons is at the interface between the electron blocking layer 124c and the emitting layer 122. This indicates that during an entire transport process (i.e., an entire process from the injection to the transport) of holes and electrons, an electron transport rate of the material of the second functional material layer 125 is greater than a hole transport rate of the material of the first functional material layer 124, which causes the recombination zones of excitons to be more biased toward the electron blocking layer 124c, resulting in accumulation of the electrons at the interface between the electron blocking layer 124c and the emitting layer 122. As a result, the materials are deteriorated by charges, and a performance of the device is further affected.

Based on this, in some embodiments, under the same test condition, the hole mobility of the material of the first functional material layer 124 is at least ten times the electron mobility of the material of the second functional material layer 125.

That is, the material of the first functional material layer 124 and the material of the second functional material layer 125 are reasonably selected, so that the hole transport rate of the material of the first functional material layer 124 and the electron transport rate of the material of the second functional material layer 125 in the organic light-emitting device 12 are adjusted in a way that the hole transport rate in the organic light-emitting device 12 is accelerated, and the electron transport rate in the organic light-emitting device 12 is reduced. As a result, the recombination zones are adjusted such that the recombination zones shift to a region of the emitting layer 122 away from the electron blocking layer 124c, which reduces accumulation of the excitons at the interface between the electron blocking layer 124c and the emitting layer 122, and avoids the accumulation of the electrons at the interface between the electron blocking layer 124c and the emitting layer 122. Therefore, it is possible to slow down the deterioration of the materials caused by accumulation of the charges, so that a stability of the device can be improved and a service life of the device can be improved.

In some embodiments, according to a case where the first functional material layer 124 includes the hole inject layer 124a, the hole transport layer 124b, and the electron blocking layer 124c, it will be seen that as for the first functional material layer 124, in a case where a material of the hole inject layer 124a is certain, materials of the hole transport layer 124b and the electron blocking layer 124c are the same or different. In a case where the materials of the hole transport layer 124b and the electron blocking layer 124c are the same, a hole mobility of the material of the hole transport layer 124b is the same as a hole mobility of the material of the electron blocking layer 124c. In a case where the materials of the hole transport layer 124b and the electron blocking layer 124c are different, the hole mobility of the material of the hole transport layer 124b is different from the hole mobility of the material of the electron blocking layer 124c. In this case, the hole mobility of the material of the electron blocking layer 124c is generally less than the hole mobility of the material of the hole transport layer 124b. In order to improve the hole transport rate as much as possible, for example, under the same test condition, the hole mobility of the material of the electron blocking layer 124c is not less than one tenth of the hole mobility of the material of the hole transport layer 124b.

In some embodiments, under the test condition of the electric field intensity of 5000 $V^{1/2}/m^{1/2}$, the hole mobility of the material of the hole transport layer 124b is $10^{-6}$ $cm^2V^{-1}s^{-1}$ to 10 $cm^2V^{-1}s^{-1}$, inclusive; and the hole mobility of the material of the electron blocking layer 124c is $10^{-7}$ $cm^2V^{-1}s^{-1}$ to $10^{-4}$ $cm^2V^{-1}s^{-1}$, inclusive.

For example, the hole mobilities of the materials of the hole transport layer 124b and the electron blocking layer 124c may be tested adopting the SCLC method.

According to the case where the hole mobility of the material of the first functional material layer 124 is at least ten times the electron mobility of the material of the second functional material layer 125, it will be seen that, in a case where the hole mobility of the material of the first functional material layer 124 is $10^{-4}$ $cm^2V^{-1}s^{-1}$, the electron mobility of the material of the second functional material layer 125 is less than or equal to $10^{-5}$ $cm^2V^{-1}s^{-1}$; in a case where the hole mobility of the material of the first functional material layer 124 is $10^{-5}$ $cm^2V^{-1}s^{-1}$, the electron mobility of the material of the second functional material layer 125 is less than or equal to $10^{-6}$ $cm^2V^{-1}s^{-1}$; and by analogy, in a case where the hole mobility of the material of the first functional material layer 124 is $10^{-6}$ $cm^2V^{-1}s^{-1}$, the electron mobility of the material of the second functional material layer 125 is less than or equal to $10^{-7}$ $cm^2V^{-1}s^{-1}$.

The first functional material layer 124 includes the hole transport layer 124b and the electron blocking layer 124c, and in the case where the hole mobility of the material of the hole transport layer 124b is different from the hole mobility of the material of the electron blocking layer 124c, the hole mobility of the material of the electron blocking layer 124c is generally less than the hole mobility of the material of the hole transport layer 124b, and the hole mobility of the material of the electron blocking layer 124c is not less than one tenth of the hole mobility of the material of the hole transport layer 124b. It will be seen from the above that in the case where the hole mobility of the material of the first functional material layer 124 is at least ten times the electron mobility of the material of the second functional material layer 125, the comparison is made based on a larger hole mobility in the first functional material layer 124. For example, in a case where the hole mobility of the material of the hole transport layer 124b in the first functional material layer 124 is $10^{-4}$ $cm^2V^{-1}s^{-1}$, and the hole mobility of the material of the electron blocking layer 124c in the first functional material layer 124 is $10^{-5}$ $cm^2V^{-1}s^{-1}$, the hole mobility of the material of the hole transport layer 124b in the first functional material layer 124 is at least ten times the electron mobility of the material of the second functional material layer 125. In this case, the electron mobility of the material of the second functional material layer 125 is less than or equal to $10^{-5}$ $cm^2V^{-1}s^{-1}$.

In this case, according to the case where the second functional material layer 125 includes the electron inject layer 125a, the electron transport layer 125b, and the hole blocking layer 125c, it will be seen that as for the second functional material layer 125, in a case where a material of the electron inject layer 125a is certain, materials of the electron transport layer 125b and the hole blocking layer 125c may also be the same or different. In a case where the materials of the electron transport layer 125b and the hole blocking layer 125c are the same, an electron mobility of the material of the electron transport layer 125b is the same as an electron mobility of the material of the hole blocking layer 125c. In a case where the materials of the electron transport layer 125b and the hole blocking layer 125c are different, the electron mobility of the material of the electron transport layer 125b is different from the electron mobility of the material of the hole blocking layer 125c. In this case, the electron mobility of the material of the hole blocking layer 125c is less than the electron mobility of the material of the electron transport layer 125b.

In the above, the comparison is made based on the larger hole mobility in the first functional material layer 124 when the hole mobility of the material of the first functional material layer 124 is compared with the electron mobility of the material of the second functional material layer 125, and in the second functional material layer 125, the electron mobility of the material of the hole blocking layer 125c is less than the electron mobility of the material of the electron transport layer 125b. In a case where the materials of the hole blocking layer 125c and the electron transport layer 125b in the second functional material layer 125 are different, a larger electron mobility in the second functional material layer 125 is also used when the hole mobility of the material of the first functional material layer 124 is compared with the electron mobility of the material of the second functional material layer 125.

That is, in a case where the material of the first functional material layer 124 is certain, that the hole mobility of the material of the first functional material layer 124 is at least ten times the electron mobility of the material of the second functional material layer 125 means that the hole mobility of the material of the first functional material layer 124 is at least ten times the electron mobility of the electron transport layer 125b. In the specific case where the first functional material layer 124 includes the hole transport layer 124b and the electron blocking layer 124c, and the second functional material layer 125 includes the electron transport layer 125b and the hole blocking layer 125c, the hole mobility of the material of the hole transport layer 124b is at least ten times the electron mobility of the electron transport layer 125b. Herein, still considering the hole mobility of the material of the hole transport layer 124b being $10^{-4}$ $cm^2V^{-1}s^{-1}$ as an example, the electron mobility of the material of the electron transport layer 125b is less than or equal to $10^{-5}$ $cm^2V^{-1}s^{-1}$, and in this case, the electron mobility of the material of the hole blocking layer 125c is less than $10^{-5}$ $cm^2V^{-1}s^{-1}$. For example, it may be $10^{-6}$ $cm^2V^{-1}s^{-1}$.

In some embodiments, under the test condition of the electric field intensity of 5000 $V^{1/2}/m^{1/2}$, the electron mobility of the material of the electron transport layer 125b is $10^{-7}$ $cm^2V^{-1}s^{-1}$ to $10^{-5}$ $cm^2V^{-1}s^{-1}$, inclusive, and the electron mobility of the material of the hole blocking layer 125c is $10^{-9}$ cm$^2$V$^{-1}$s$^{-1}$ to $10^{-7}$ cm$^2$V$^{-1}$s$^{-1}$, inclusive. That is, still under the test condition of the electric field intensity of 5000 V$^{1/2}$/m$^{1/2}$, in a case where the hole mobility of the hole transport layer 124b is $10^{-6}$ cm$^2$V$^{-1}$s$^{-1}$ to $10^{-4}$ cm$^2$V$^{-1}$s$^{-1}$, inclusive, and the hole mobility of the material of the electron blocking layer 124c is $10^{-7}$ cm$^2$V$^{-1}$s$^{-1}$ to $10^{-4}$ cm$^2$V$^{-1}$s$^{-1}$, inclusive, the electron mobility of the material of the electron transport layer 125b is any value from $10^{-7}$ cm$^2$V$^{-1}$s$^{-1}$ to $10^{-5}$ cm$^2$V$^{-1}$s$^{-1}$, inclusive, and the electron mobility of the material of the hole blocking layer 125c is any value from $10^{-9}$ cm$^2$V$^{-1}$s$^{-1}$ to $10^{-7}$ cm$^2$V$^{-1}$s$^{-1}$, inclusive. It is possible to increase the hole transport rate, reduce the electron transport rate, and improve an efficiency and the service life of the device.

In some embodiments, the hole transport layer 124b and the electron blocking layer 124c are each independently selected from any of aromatic amine compounds. The aromatic amine compounds have good hole transport properties, and as the number of aromatic amines increases, the hole mobility becomes faster.

For example, the material of the hole transport layer 124b may be selected from the aromatic amine compounds, such as N,N'-Bis(naphthalen-1-yl)-N,N'-bis(phenyl)benzidine (NPB), 4,4',4''-Tris(N-3-methylphenyl-N-phenylamino)triphenylamine (m-MTDATA), and N,N'-diphenyl-N,N'-bis(3-methylphenyl)-[1,1'-biphenyl]-4,4'-diamine (TPD). The material of the electron blocking layer 124c may be selected from 3,3'-Di(9H-carbazol-9-yl)biphenyl (mCBP), 3,6-Bis (N-phenyloxazol-3-yl)-N-phenylcarbazole (Tris-PCz), etc.

Figure 3:
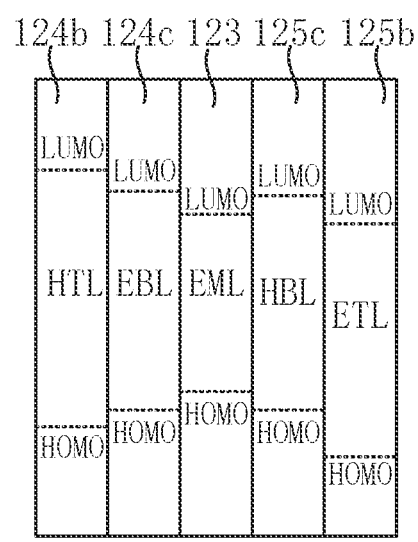
FIG. 3 is a diagram showing a relationship between HOMO energy levels and LUMO energy levels of a hole transport layer, an electron blocking layer, an emitting layer, a hole blocking layer, and an electron transport layer, in accordance with some embodiments.

In a case where the hole mobilities of the hole transport layer 124b and the electron blocking layer 124c in the first functional material layer 124 are certain, in order to further increase the hole transport rate, for example, as shown in FIG. 3, a difference between a highest occupied molecular orbital (HOMO) energy level of the hole transport layer 124b and a HOMO energy level of the material of the electron blocking layer 124c is greater than or equal to −0.5 eV, and is less than or equal to 0.3 eV, which may eliminate the slow hole transport rate caused by an energy level barrier.

In some embodiments, the material of the hole inject layer 124a may be selected from MoO$_3$, 2,3,5,6-Tetrafluoro-7,7,8,8-tetracyanoquinodimethane (F4-TCNQ), dipyrazino[2,3f:2',3'-h]quinoxaline-2,3,6,7,10,11-hexacarbonitrile (HAT-CN), etc. A thickness of the hole inject layer 124a may be 5 nm to 30 nm, inclusive, a thickness of the hole transport layer 124b may be 1000 nm to 1300 nm, inclusive, and a thickness of the electron blocking layer 124c may be 10 nm to 80 nm, inclusive.

In some embodiments, a lowest triplet exciton energy T1 of the material of the hole transport layer 124b is greater than a lowest triplet exciton energy T1 of the material of the electron blocking layer 124c.

According to a recombination mechanism of electrons and holes, in order to avoid a case where the electrons are quenched on a surface of the anode after passing through the electron blocking layer 124c because the electron blocking layer 124c is too thin, by making the lowest triplet exciton energy of the material of the hole transport layer 124b greater than the lowest triplet exciton energy of the material of the electron blocking layer 124c, it is possible to further block the electrons through the hole transport layer 124b after the electrons pass through the electron blocking layer 124c.

In some embodiments, in a case where the host material and the dopant material of the emitting layer 122 are certain, in order to further increase the hole transport rate, for example, a difference between a HOMO energy level of the host material and a HOMO energy level of the material of the electron blocking layer 124c is less than or equal to 0.3 eV, which can also improve the slow hole transport rate caused by the energy level barrier.

In some embodiments, the lowest triplet exciton energy T1 of the material of the electron blocking layer 124c is greater than a lowest triplet exciton energy T1 of the host material.

Similarly, by making the lowest triplet exciton energy of the material of the electron blocking layer 124c greater than the lowest triplet exciton energy of the host material, it is possible to confine the triplet excitons in the emitting layer 122 to effectively utilize the triplet excitons.

Herein, in an example in which the organic light-emitting device is the light-emitting device that emits blue light, in some embodiments, the host material of the emitting layer 122 may be selected from 9,10-di(2-naphthyl)anthracene (AND), 2-(tert-Butyl)-9,10-di(2-naphthalenyl)anthracene (TBADN), 2-Methyl-9,10-bis(naphthalen-2-yl)anthracene (MADN), 1,3,5-Tri-(pyren-1-yl)-benzene (TPB3), etc. The dopant material may be selected from 4,4'-Bis(2,2-diphenylvinyl)-1,1'-biphenyl (Dpvbi). A thickness of the emitting layer 122 may be 20 nm to 40 nm, inclusive.

In some embodiments, the material of the electron transport layer 125b and the material of the hole blocking layer 125c are each independently selected from compounds containing at least one heteroaryl which contains at least two N atoms, such as 2,9-Dimethyl-4,7-diphenyl-1,10-phenanthroline (BCP), 1,10-Phenanthroline monohydrate (Bphen), azine, etc. These compounds have good electron transport properties.

In some embodiments, the material of the electron transport layer 125b may be a compound based on a spirocyclic aromatic hydrocarbon structure. That is, the material of the electron transport layer 125b is selected from compounds having a spirocyclic aromatic hydrocarbon structure (e.g., spirofluorene, or spirofluorene xanthene). In this case, in one aspect, the spirocyclic aromatic hydrocarbon has a good electron withdrawing property, which may further improve an electron transport property of the electron transport layer 125b. In another aspect, the spirocyclic aromatic hydrocarbon structure has a relatively high T1 and is a group with a good steric configuration, which may suppress crystallization of the material to a certain extent. In this way, in a case where the host material of the emitting layer 122 and the material of the hole blocking layer 125c are certain, it is also possible to confine the triplet excitons to a region proximate to the emitting layer 122, so as to further block the electrons and prevent the electrons from being quenched.

In some embodiments, the material of the electron transport layer 125b is selected from any one or a combination of two or more of structures shown in a general formula (I):

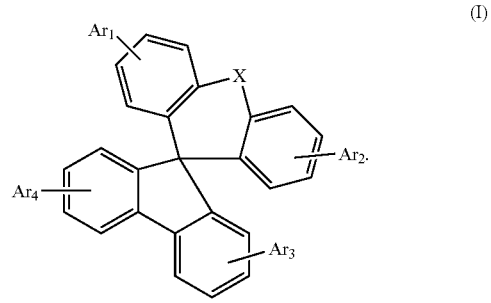

(I)

In the general formula (I), X is selected from any of C(R)$_2$, O, S, N(R), and a single bond. In a case where X is selected from the single bond, the general formula (I) is spirofluorene. Ar$_1$ to Ar$_4$ may exist simultaneously or separately, and are each independently selected from aryl or heteroaryl with 5 to 30 ring atoms substituted or unsubstituted by a substituent R$_1$, at least one of Ar$_1$ to Ar$_4$ is selected from any of structures shown in a following general formula (II), and the substituent R$_1$ is selected from any of tert-butyl, cyano, aryl or heteroaryl with 5 to 30 ring atoms, and —Y$_1$(Ar)$_n$.

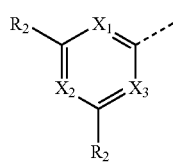
(II)

In the general formula (II), X$_1$, X$_2$, and X$_3$ are each independently selected from any of C(R$_2$) and N, and at least two of X$_1$, X$_2$, and X$_3$ are selected from N. Each R$_2$ is the same or different, and is independently selected from any of H and aryl or heteroaryl with 5 to 30 ring atoms. In a case where R2 is selected from the aryl or heteroaryl with 5 to 30 ring atoms, the aryl or heteroaryl has or has no the substituent R$_1$. Y$_1$ is selected from any of carbon, nitrogen, phosphorus, silicon, boron, C(R$_3$)$_2$, Si(R$_3$)$_2$, C(=O), C(=NR), C(=C(R)$_2$), S(=O), S(=O)$_2$, and P(=O), and n is an integer greater than or equal to 1. Each Ar is the same or different, and is independently selected from the aryl or heteroaryl. Alternatively, in a case where n is an integer greater than or equal to 2, at least two Ars are connected into a ring through a single bond or a first bridging group, and the first bridging group is selected from B(R), C(R)$_2$, Si(R)$_2$, C(=O), C(=NR), C(=C(R)$_2$), O, S, S(=O), S(=O)$_2$, N(R), P(R), and P(=O)(R). R$_3$ is selected from any of H and methyl, and R is selected from any of H, methyl, aryl or heteroaryl.

According to the case where in the general formula (II), X$_1$, X$_2$, and X$_3$ are each independently selected from any of C(R$_2$) and N, and at least two of X$_1$, X$_2$, and X$_3$ are selected from N, it will be seen that the general formula (II) is a general formula of azine. In this case, in an example in which Ar$_3$ in the general formula (I) is selected from the general formula (II), Ar$_4$ is selected from phenyl substituted by the substituent R$_1$, and Ar$_1$ and Ar$_2$ do not exist, a structural formula of the general formula (I) may be expressed as follows.

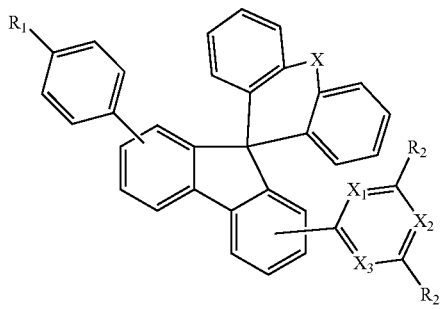

In this case, in an example in which X$_1$, X$_2$, and X$_3$ are all selected from N, according to a case where R$_2$ may be selected from any of H and aryl or heteroaryl with 5 to 30 ring atoms, and the aryl or heteroaryl has or has no the substituent R1 in a case where R$_2$ is selected from the aryl or heteroaryl with 5 to 30 ring atoms, it will be seen that the general formula (I) may be selected from any of following compounds:

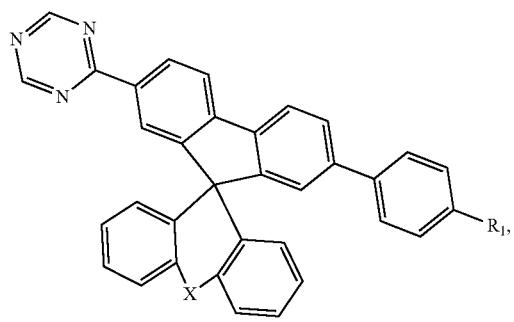

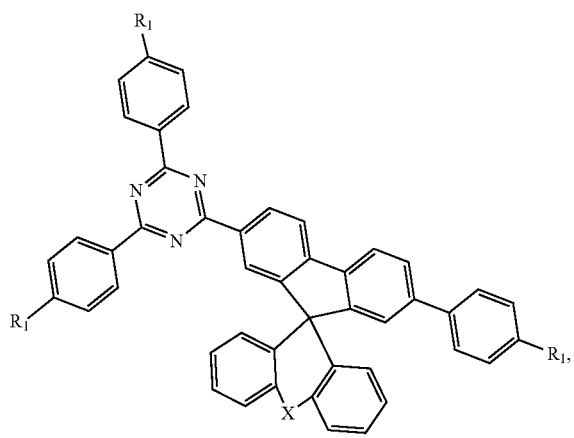

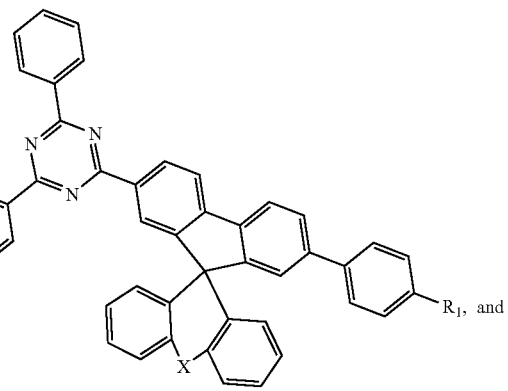

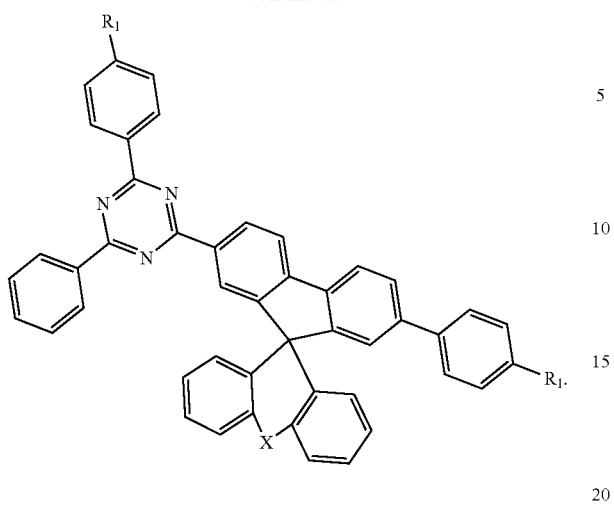

According to a case where X may be selected from any of C(R)$_2$, O, S, N(R), and the single bond, and R$_1$ is independently selected from any of the tert-butyl, cyano, aryl or heteroaryl with 5 to 30 ring atoms, and —Y$_1$(Ar)$_n$, it will be seen that the general formula (I) may be selected from any of following compounds. In this case, the material of the electron transport layer may be selected from any one or a combination of two or more of following compounds:

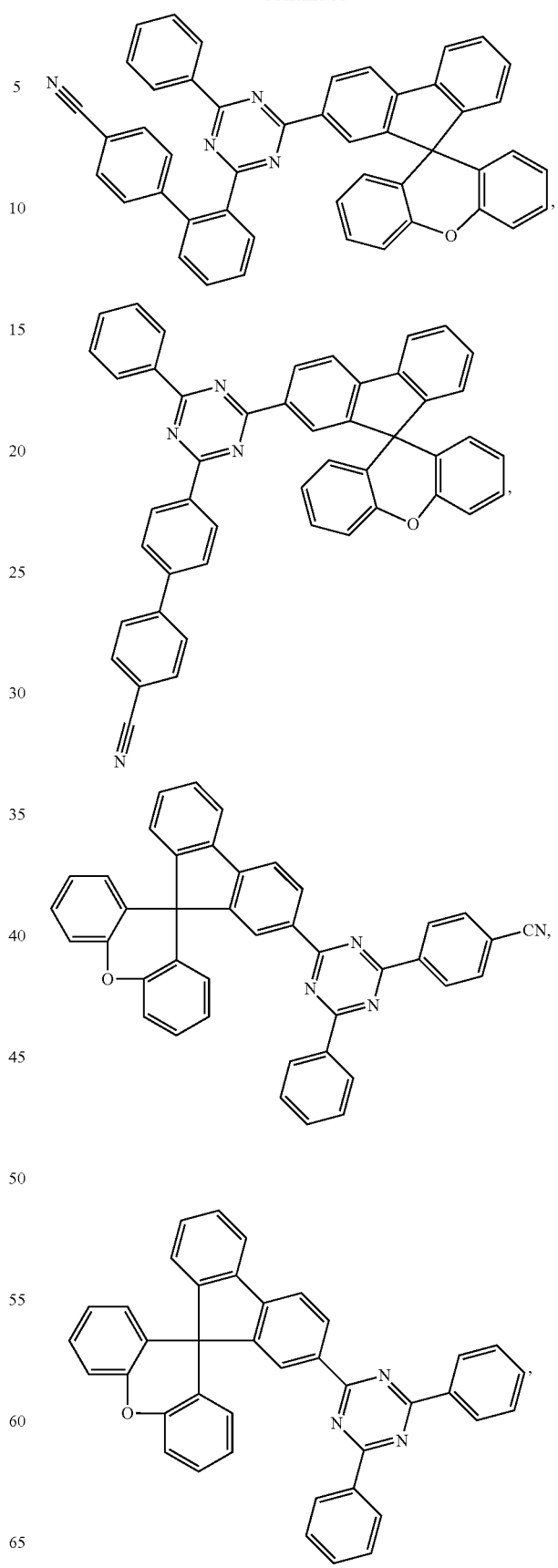

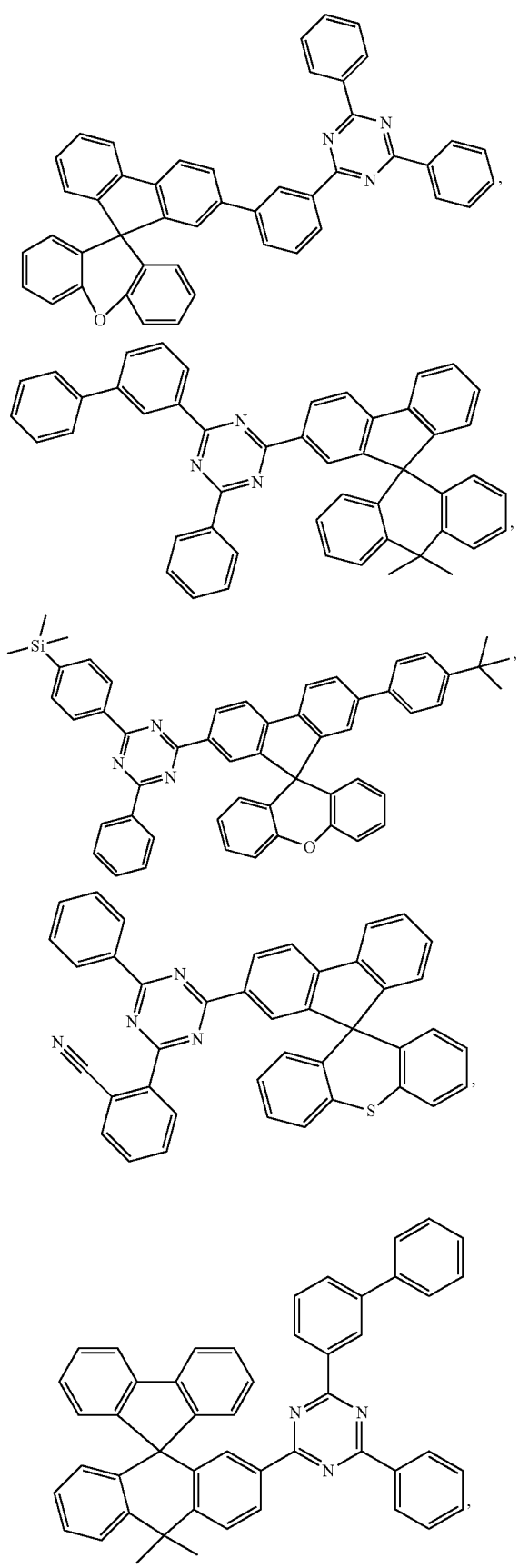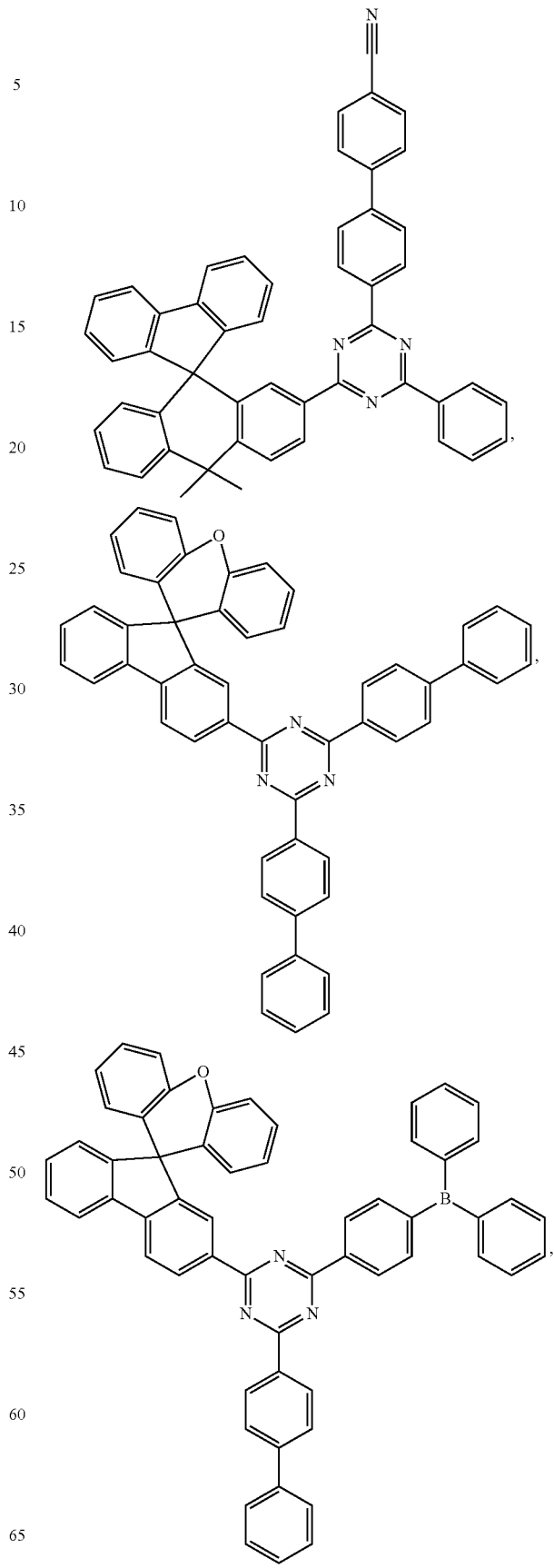

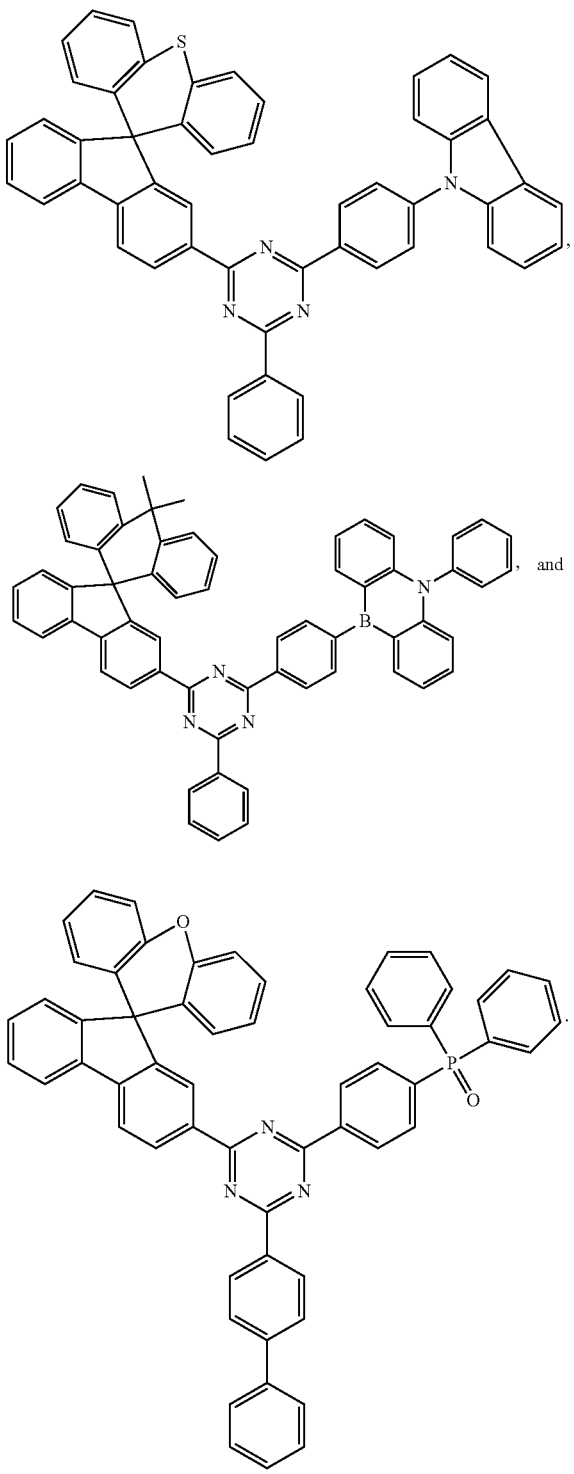

Herein, it will be noted that the compounds shown above are only examples. Herein, those skilled in the art will understand that all the compounds cannot be exhaustively listed, and combinations that meet the above description are all within the protection scope of the present disclosure.

In some embodiments, the material of the hole blocking layer 125c is selected from any one or a combination of two or more of structures shown in a general formula (III).

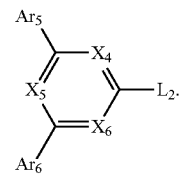

(III)

In the general formula (III), $X_4$, $X_5$, and $X_6$ are each independently selected from any of C(R) and N, and at least two of $X_4$, $X_5$, and $X_6$ are selected from N. $Ar_5$, $Ar_6$, and $L_2$ are each independently selected from aryl with 6 to 60 carbon atoms substituted or unsubstituted by a substituent $R_1$, or heteroaryl with 2 to 60 carbon atoms substituted or unsubstituted by the substituent $R_1$. $L_1$ is selected from a single bond, divalent aryl with 6 to 60 carbon atoms substituted or unsubstituted by the substituent $R_1$, or divalent heteroaryl with 2 to 60 carbon atoms substituted or unsubstituted by the substituent $R_1$. $R_1$ is independently selected from any of test-butyl, cyano, aryl or heteroaryl with 5 to 30 ring atoms, and $-Y_1(Ar)_n$. $Y_1$ is selected from any of carbon, nitrogen, phosphorus, silicon, boron, $C(R_3)_2$, $Si(R_3)_2$, $C(=O)$, $C(=NR)$, $C(=C(R)_2)$, $S(=O)$, $S(=O)_2$, and $P(=O)$, and n is an integer greater than or equal to 1. Each Ar is the same or different, and is independently selected from the aryl or heteroaryl. Alternatively, Ar and the aryl or heteroaryl substituted by the substituent R1 are connected into a ring through a single bond or a second bridging group, and/or in a case where n is an integer greater than or equal to 2, at least two Ars are connected into a ring through a single bond or a second bridging group. The second bridging group is selected from B(R), $C(R)_2$, $Si(R)_2$, $C(=O)$, $C(=NR)$, $C(=C(R)_2)$, O, S, $S(=O)$, $S(=O)_2$, N(R), P(R), and $P(=O)(R)$. $R_3$ is selected from any of H and methyl, and R is selected from any of H, methyl, aryl and heteroaryl.

According to the case where $Ar_5$, $Ar_6$, and $L_2$ are each independently selected from the aryl with 6 to 60 carbon atoms substituted or unsubstituted by the substituent $R_1$, or the heteroaryl with 2 to 60 carbon atoms substituted or unsubstituted by the substituent $R_1$, it will be seen that $Ar_5$, $Ar_6$, and $L_2$ may each be independently selected from any of phenyl, biphenyl, naphthyl, anthryl, fluorenyl, spirocyclic aryl, thienyl, pyridyl, quinolyl, imidazolyl, indolyl, benzofuranyl, and benzothiophene that are each substituted or unsubstituted by the substituent $R_1$.

According to the case where $L_1$ is selected from the single bond, the divalent aryl with 6 to 60 carbon atoms substituted or unsubstituted by the substituent $R_1$, or the divalent heteroaryl with 2 to 60 carbon atoms substituted or unsubstituted by the substituent $R_1$, it will be seen that in a case where $L_1$ is selected from the single bond, the general formula (III) may be expressed as:

In a case where $L_1$ is selected from the divalent aryl with 6 to 60 carbon atoms substituted or unsubstituted by the substituent $R_1$, or the divalent heteroaryl with 2 to 60 carbon atoms substituted or unsubstituted by the substituent $R_1$, $L_1$ may be selected from any of divalent phenyl, divalent biphenyl, divalent naphthyl, divalent anthryl, divalent fluorenyl, divalent spirocyclic aryl, divalent thienyl, divalent pyridyl, divalent quinolinyl, divalent imidazolyl, divalent indolyl, divalent benzofuranyl, and divalent benzothiophene that are each substituted or unsubstituted by the substituent $R_1$.

In some embodiments, in the general formula (III), in a case where $L_1$ is selected from divalent bicyclic aryl substituted or unsubstituted by the substituent $R_1$, at least one single ring in the divalent bicyclic aryl has a group attached at a meta position and/or an ortho position. In a case where $L_1$ is selected from monocyclic aryl substituted or unsubstituted by the substituent $R_1$, $L_2$ and azine are attached at a meta position or an ortho position of $L_1$.

That at least one single ring in the divalent bicyclic aryl has a group attached at the meta position and/or the ortho position means that there is a substituent $R_1$ in the meta position and/or the ortho position of the at least one single ring in the divalent bicyclic aryl, or the remaining aromatic rings in the divalent bicyclic aryl apart from the single ring are attached at the meta position and/or the ortho position of the single ring, or the remaining aromatic rings and the azine in the divalent bicyclic aryl apart from the single ring are attached at the meta position and/or the ortho position of the single ring, or the remaining aromatic rings and the substituent $R_1$ in the divalent bicyclic aryl apart from the single ring are attached at the meta position and/or the ortho position of the single ring, or the substituent $R_1$ and the azine in the divalent bicyclic aryl are attached at the meta position and/or the ortho position of the single ring.

For example, in an example in which $L_1$ is selected from the unsubstituted biphenyl, the general formula (III) may be selected from any of following structures:

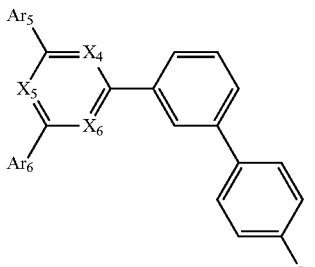

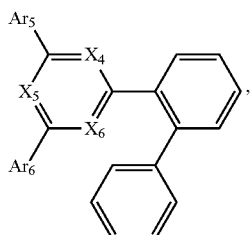

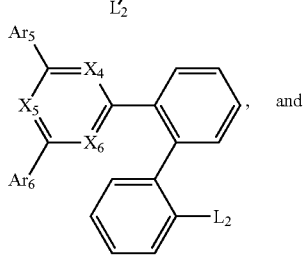

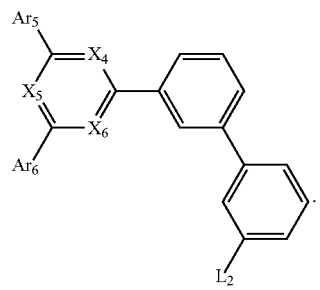

In an example in which $L_1$ is selected from the biphenyl substituted by the substituent the general formula (III) may be selected from any of following structures:

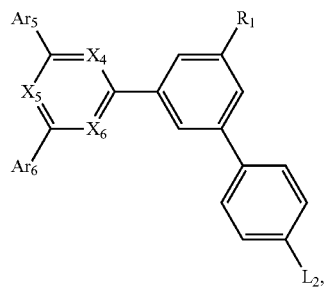

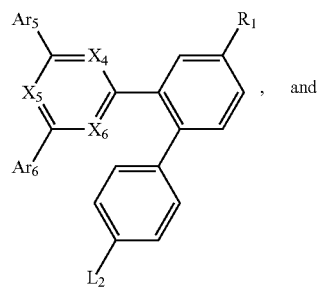

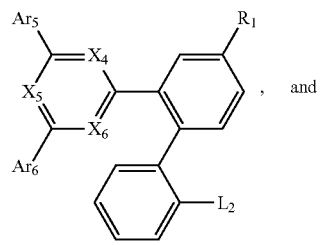

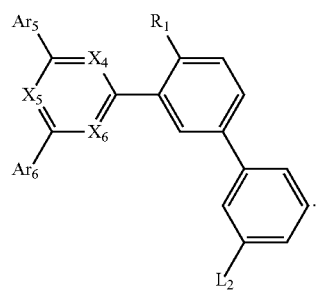

In an example in which $L_1$ is selected from unsubstituted monocyclic aryl, the general formula (III) may be selected from any of following structures:

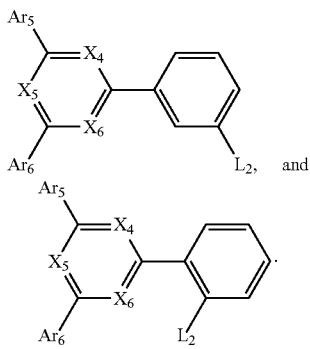

In an example in which $L_1$ is selected from the monocyclic aryl substituted by the substituent $R_1$, the general formula (III) may be selected from any of following structures:

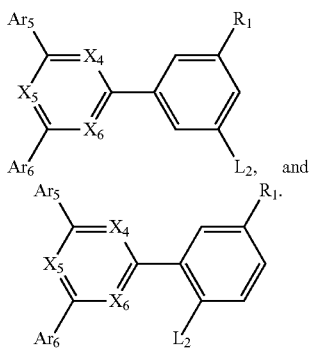

In the above structures, by arranging the meta-position or ortho-position connection among the groups, it may greatly increase the steric twist of molecules to a great extent, and reduce a degree of conjugation of the molecules, thus reducing the mobility of the material and helping to slow down the transport of electrons. In addition, a compound with a large steric twist has a relatively high T1, which may confine the triplet excitons in the emitting layer 122, and can suppress the crystallization of the material to a certain extent.

In the above description, $R_1$ is independently selected from any of tert-butyl, cyano, aryl or heteroaryl with 5 to 30 ring atoms, and $-Y_1(Ar)_n$, $Y_1$ is selected from any of carbon, nitrogen, phosphorus, silicon, boron, $C(R_3)_2$, $Si(R_3)_2$, $C(=O)$, $C(=NR)$, $C(=C(R)_2)$, $S(=O)$, $S(=O)_2$, and $P(=O)$, n is the integer greater than or equal to 1, each Ar is the same or different, and is independently selected from the aryl or heteroaryl, or Ar and the aryl or heteroaryl substituted by the substituent $R_1$ are connected as the ring through the single bond or the second bridging group, and/or at least two Ars, in a case where n is the integer greater than or equal to 2, are connected as the ring through the single bond or the second bridging group, the second bridging group is selected from $B(R)$, $C(R)_2$, $Si(R)_2$, $C(=O)$, $C(=NR)$, $C(=C(R)_2)$, O, S, $S(=O)$, $S(=O)_2$, $N(R)$, $P(R)$, and $P(=O)(R)$, $R_3$ is selected from any of H and methyl, and R is selected from any of H, methyl, aryl and heteroaryl. The aryl or heteroaryl with 5 to 30 ring atoms is referred to as A. It will be seen from the above that in a case where $L_2$ is selected from the aryl or heteroaryl with 5 to 30 ring atoms substituted by the substituent $R_1$, and $R_1$ is selected from $-Y_1(Ar)_n$, a structural formula of $L_2$ may be as shown below, and $L_2$ is connected to $L_1$ by a dotted line.

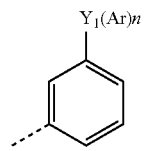

In an example in which A is selected from benzene ring, Ar is selected from benzene ring, $Y_1$ is selected from $C(R_3)_2$, $R_3$ is selected from methyl, and in this case, n is equal to 1, and Ar and A are connected as a ring through a single bond, the structural formula of $L_2$ may be expressed as follows.

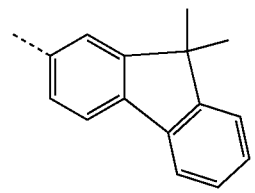

In an example in which A is selected from benzene ring, Ar is selected from benzene ring, $Y_1$ is selected from carbon, and in this case, n is equal to 3, the structural formula of $L_2$ may be expressed as follows.

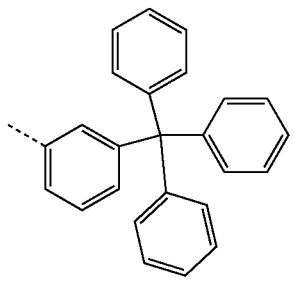

In an example in which A is selected from benzene ring, Ar is selected from benzene ring, $Y_1$ is selected from carbon, and in this case, n is equal to 3, and one Ar and A are connected as a ring through a single bond, the structural formula of $L_2$ may be expressed as follows.

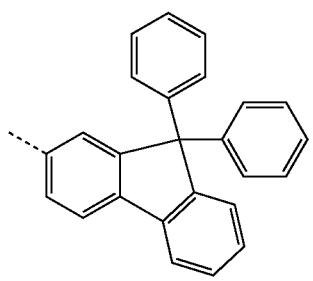

In an example in which A is selected from benzene ring, $Y_1$ is selected from nitrogen, Ar is selected from benzene ring, and in this case, n is equal to 2, and two Ars are connected as a ring through a single bond, the structural formula of $L_2$ may be expressed as follows.

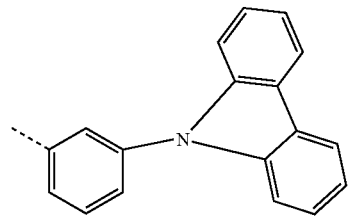

In an example in which A is selected from benzene ring, $Y_1$ is selected from O, Ar is selected from benzene ring, and in this case, n is equal to 1, and Ar and A are connected as a ring through a single bond, a structural formula of $L_2$ may be expressed as follows.

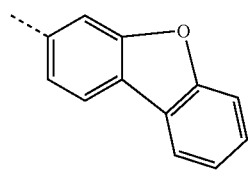

In the above structural formulas, by introducing an atom with relatively large steric configuration such as boron, phosphorus, sulfur, or silicon into the general formula (III), it is possible to increase the steric configuration of the molecule, and make the steric twist of the molecule large, which is beneficial to improve T1. In addition, by introducing an electron-withdrawing group such as boron, nitrogen, sulfur, or phosphorus, it is also possible to increase the electron mobility.

In some embodiments, the material of the hole blocking layer 125c is selected from any one or a combination of two or more of following structures:

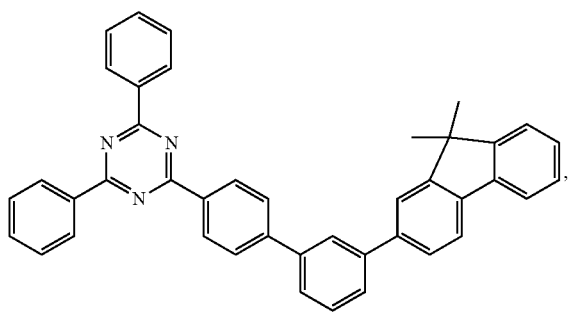

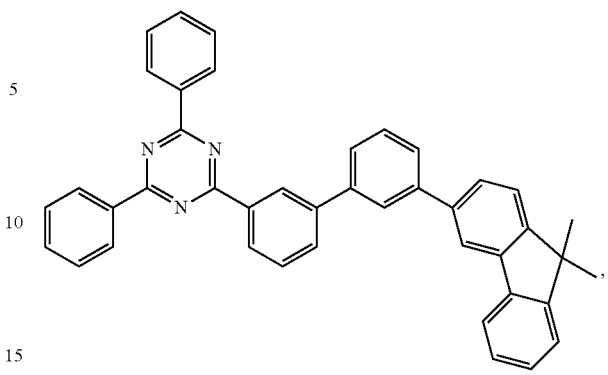

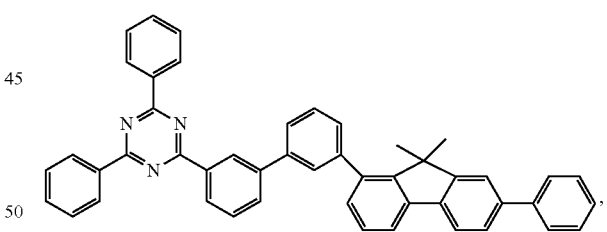

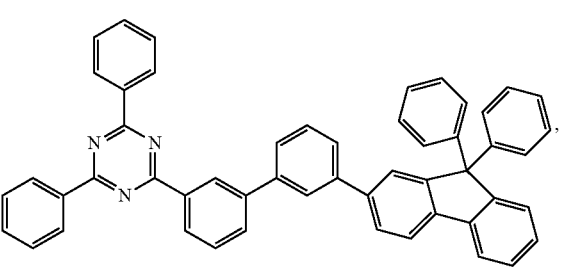

-continued

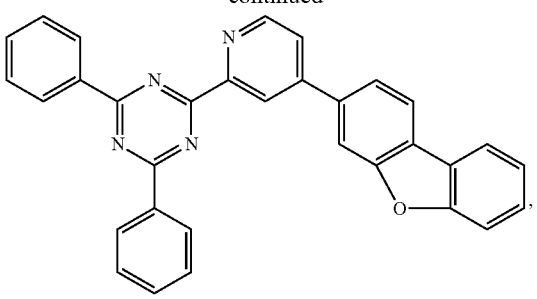

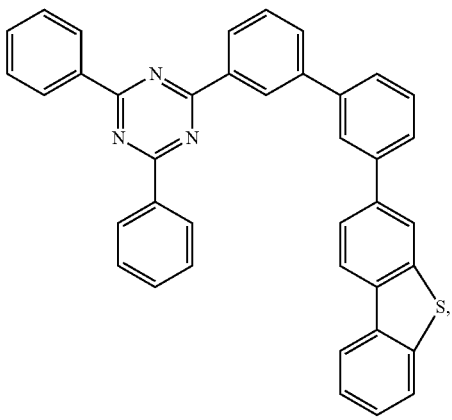

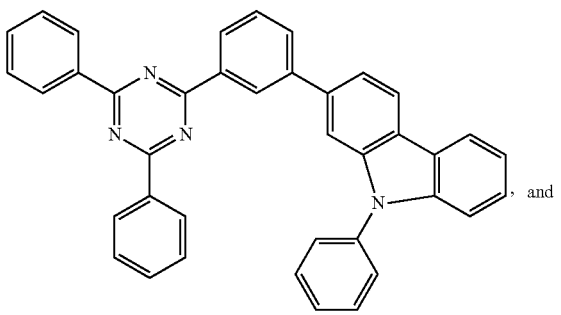

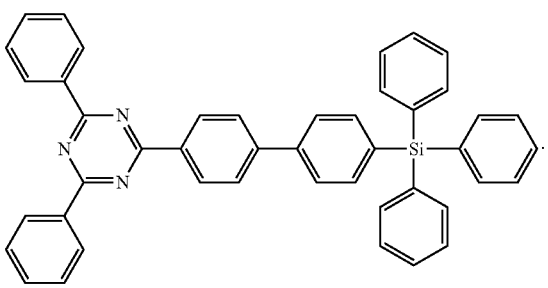

Based on the above structures, in a case where the electron mobilities of the electron transport layer 125b and the hole blocking layer 125c in the second functional material layer 125 are certain, in order to further reduce the electron transport rate, for example, a difference between a lowest unoccupied molecular orbital (LUMO) energy level of the hole blocking layer 125c and a LUMO energy level of the electron transport layer 125b is greater than or equal to 0.4 eV, and is less than or equal to 1 eV, which may increase an energy level barrier between the hole blocking layer 125c and the electron transport layer 125b, so as to further reduce the electron transport rate.

In some embodiments, the material of the electron inject layer 125a may be selected from alkali metals or metals, such as LiF, Yb, and 8-hydroxyquionline lithium (LiQ). A thickness of the electron inject layer 125a may be 1 nm to 3 nm, inclusive, a thickness of the electron transport layer 125b may be 20 to 35 nm, inclusive, and a thickness of the hole blocking layer 125c may be 5 nm to 10 nm, inclusive.

In some embodiments, a lowest triplet exciton energy T1 of the material of the electron transport layer 125b is greater than a lowest triplet exciton energy T1 of the material of the hole blocking layer 125c.

According to the recombination mechanism of electrons and holes, in order to avoid a case where the holes are quenched on a surface of the cathode after passing through the hole blocking layer 125c because the hole blocking layer 125c is too thin, the lowest triplet exciton energy of the material of the electron transport layer 125b is made greater than the lowest triplet exciton energy of the material of the hole blocking layer 125c, which is also possible to further block the holes through the electron transport layer 125b after the holes pass through the hole blocking layer 125c, thereby preventing the holes from being quenched.

In some embodiments, in order to further reduce the electron transport rate, a difference between a HOMO energy level of the material of the hole blocking layer 125c and a HOMO energy level of the host material of the emitting layer 122 is greater than or equal to 0.1 eV, which may well block the holes.

In some embodiments, the lowest triplet exciton energy T1 of the material of the hole blocking layer 125c is greater than the lowest triplet exciton energy T1 of the host material.

Similarly, by making the lowest triplet exciton energy of the material of the hole blocking layer 125c greater than the lowest triplet exciton energy of the host material, it is possible to confine the triplet excitons in the emitting layer 122, so as to effectively utilize the triplet excitons.

In order to objectively evaluate the technical effects of the embodiments of the present disclosure, the technical solutions will be exemplarily described in detail below through following experimental examples and comparative examples.

In the following experimental examples and comparative examples, structures and the test conditions of the devices that are adopted are the same. The structure of the device is expressed as: anode (indium tin oxide (ITO)), HIL, HTL, EBL, Host+Dopant, HBL, ETL, EIL, and cathode (Al).

A comparative example 1, a comparative example 2, a comparative example 3, a comparative example 4, a comparative example 5, an experimental example 1, an experimental example 2, an experimental example 3, and an experimental example 4 are provided. In the comparative examples 1 to 5 and the experiment examples 1 to 4, materials of the remaining layers except for the ETLs and the HBLs are the same, and selected from following structures.

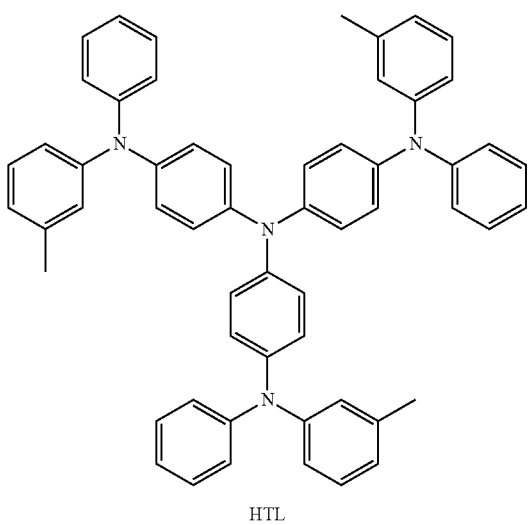

HTL

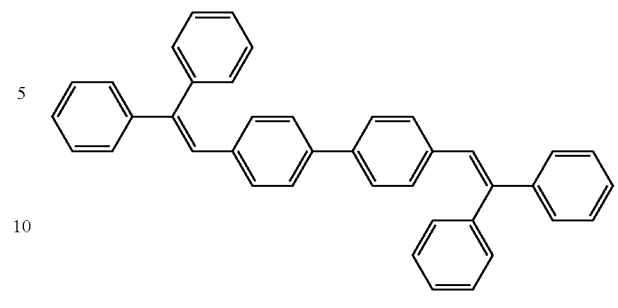

Dopant

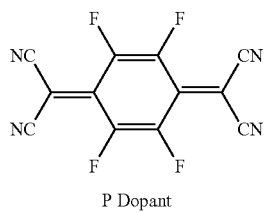

P Dopant

The material of the hole inject layer 124a is selected from a mixed material of a structural formula shown in the HTL and a structural formula shown in the P Dopant. The material of the electron inject layer 125a is selected from lithium fluoride.

In the comparative examples 1 to 5 and the experimental examples 1 to 4, the materials of the ETLs and the HBLs are selected from materials as shown in Table 1 below, respectively, The HOMO energy levels, the LIMO energy levels, and the lowest triplet energies T1 of the materials shown in Table 1 are as shown in Table 2 below. Structural formulas of the materials shown in Table 1 and names of the structural formulas are as shown below.

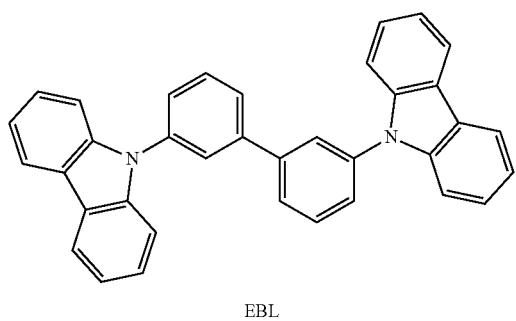

EBL

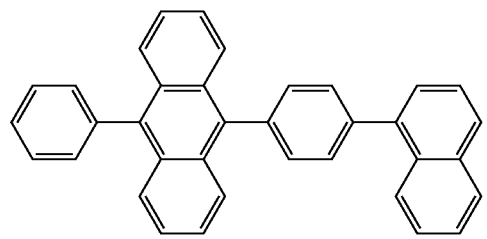

Host

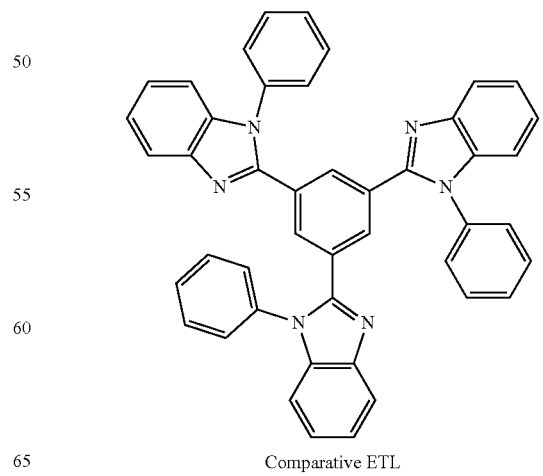

Comparative ETL

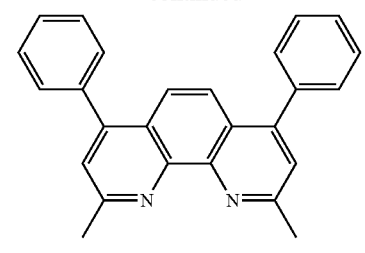

Comparative HBL

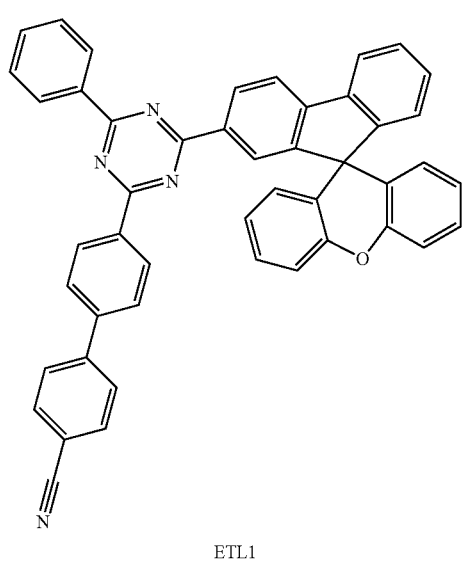

ETL1

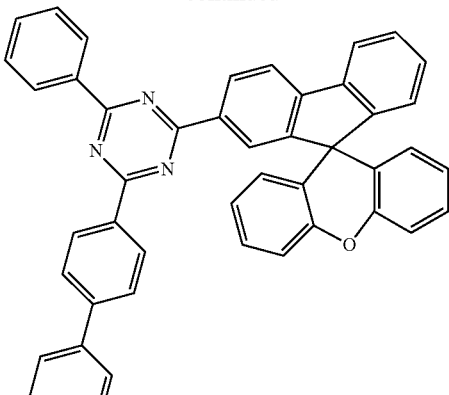

ETL2

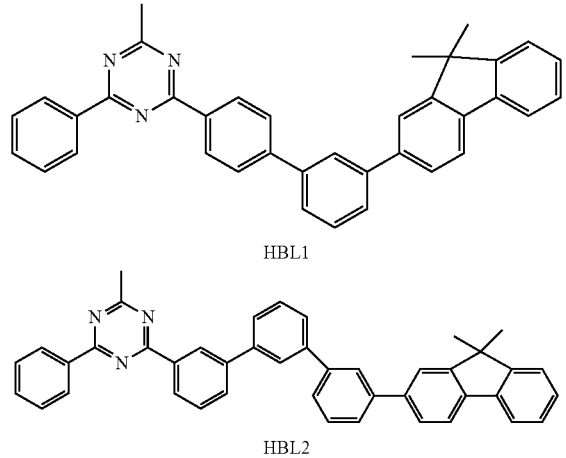

HBL1

HBL2

TABLE 1

|  | Material of ETL | Material of HBL | Voltage | Efficiency | Service life (LT95@ 1000 nit) |
| --- | --- | --- | --- | --- | --- |
| Comparative example 1 | Comparative ETL | Comparative HBL | 100% | 100% | 100% |
| Comparative example 2 | ETL1 | Comparative HBL | 100% | 102% | 120% |
| Comparative example 3 | ETL2 | Comparative HBL | 95% | 105% | 129% |
| Comparative example 4 | Comparative ETL | HBL1 | 97% | 108% | 103% |
| Comparative example 5 | Comparative ETL | HBL2 | 96% | 109% | 104% |
| Experimental example 1 | ETL1 | HBL1 | 96% | 119% | 131% |
| Experimental example 2 | ETL1 | HBL2 | 94% | 128% | 137% |
| Experimental example 3 | ETL2 | HBL1 | 99% | 121% | 126% |
| Experimental example 4 | ETL2 | HBL2 | 97% | 120% | 130% |

TABLE 2

| Name | HOMO (eV) | LUMO (eV) | T1 (eV) |
|------|-----------|-----------|---------|
| ETL1 | −6.56 | −3.5 | 2.7 |
| ETL2 | −6.50 | −3.4 | 2.75 |
| HBL1 | −6.00 | −2.71 | 2.4 |
| HBL2 | −5.80 | −2.51 | 2.80 |

Table 1 further shows test results of driving voltages, current efficiencies, and service lives of devices in the comparative examples 1 to 5 and the experimental examples 1 to 4 under a same test condition.

It will be seen from Table 1 and Table 2 that in a case where the host material of the emitting layer 122, the material of the HTL, and the material of the EBL are all certain, suitable materials of the ETL and the HBL are chosen such that the electron mobility of the material of the ETL and the electron mobility of the material of the HBL are adjusted, the electron mobility of the organic light-emitting device is appropriately reduced, the energy levels of the materials of the functional material layers are matched simultaneously, the energy level barrier of the electrons among the material of the HBL, the material of the ETL, and the host material of the emitting layer is increased, and the energy level barrier of the holes among the material of the HBL, the material of the ETL, and the host material of the emitting layer is reduced. Therefore, it is possible to generally reduce a transport velocity of electrons, increase a transport velocity of holes, and adjust the recombination zones of the holes and the electrons, so that it is possible to make the recombination zones of the holes and the electrons away from the electron blocking layer 124c. As a result, the service lives and efficiencies of the obtained devices are improved to various degrees.

It will be seen that the embodiments provided by the present disclosure can solve a defect that the recombination zones are located at the interface between the electron blocking layer 124c and the emitting layer 122 in the related art, which leads to the accumulation of the electrons at the interface between the electron blocking layer 124c and the emitting layer 122, resulting in the deterioration of the materials due to the accumulation of the charges, which is not conducive to the improvement of the efficiencies and service lives of the devices.

The foregoing descriptions are merely specific implementations of the present disclosure, but the protection scope of the present disclosure is not limited thereto. Any person skilled in the art could conceive of changes or replacements within the technical scope of the present disclosure, which shall all be included in the protection scope of the present disclosure. Therefore, the protection scope of the present disclosure shall be subject to the protection scope of the claims.

What is claimed is:

1. An organic light-emitting device, comprising:
   an anode, an emitting layer and a cathode that are stacked;
   a first functional material layer located between the emitting layer and the anode; and
   a second functional material layer located between the emitting layer and the cathode; and
   under a same test condition, a hole mobility of a material of the first functional material layer being at least ten times an electron mobility of a material of the second functional material layer;
   wherein the second functional material layer includes an electron transport layer and a hole blocking layer;
   an electron mobility of a material of the electron transport layer is the same as an electron mobility of a material of the hole blocking layer; or, under a same test condition, the electron mobility of the material of the hole blocking layer is less than the electron mobility of the material of the electron transport layer; and
   the material of the electron transport layer and the material of the hole blocking layer are each independently selected from compounds containing at least one heteroaryl which contains at least two N atoms.

2. The organic light-emitting device according to claim 1, wherein a lowest triplet energy of the material of the electron transport layer is greater than a lowest triplet energy of the material of the hole blocking layer.

3. The organic light-emitting device according to claim 1, wherein the material of the electron transport layer is a compound based on a spirocyclic aromatic hydrocarbon structure.

4. The organic light-emitting device according to claim 3, wherein
   the material of the electron transport layer is selected from any one or a combination of two or more of structures shown in a general formula (I):

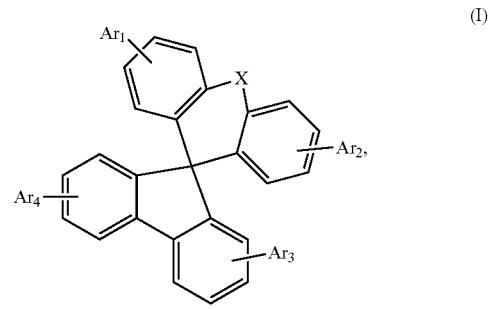

(I)

in the general formula (I), X is selected from any of $C(R)_2$, O, S, N(R), and a single bond, $Ar_1$ to $Ar_4$ are able to exist simultaneously or separately, and are each independently selected from aryl or heteroaryl with 5 to 30 ring atoms substituted or unsubstituted by a substituent R1, at least one of $Ar_1$ to $Ar_4$ is selected from any of structures shown in a following general formula (II), and the substituent $R_1$ is selected from any of tert-butyl, cyano, aryl or heteroaryl with 5 to 30 ring atoms, and $-Y_1(Ar)_n$;

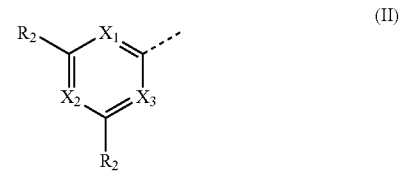

(II)

in the general formula (II), $X_1$, $X_2$, and $X_3$ are each independently selected from any of $C(R_2)$ and N, and at least two of $X_1$, $X_2$, and $X_3$ are selected from N; and each R2 is the same or different, and is independently selected from any of H and aryl or heteroaryl with 5 to 30 ring atoms, and in a case where $R_2$ is selected from the aryl or heteroaryl with 5 to 30 ring atoms, the aryl or heteroaryl has or has no the substituent $R_1$;

wherein $Y_1$ is selected from carbon, nitrogen, phosphorus, silicon, boron, $C(R_3)_2$, $Si(R_3)_2$, C(=O), C(=NR), C(=C(R)$_2$), S(=O), S(=O)$_2$, and P(=O), n is an integer greater than or equal to 1, each Ar is the same or different, and is independently selected from aryl or heteroaryl, or in a case where n is an integer greater than or equal to 2, at least two Ars are connected as a ring through a single bond or a first bridging group, and the first bridging group is selected from B(R), $C(R)_2$, $Si(R)_2$, C(=O), C(=NR), C(=C(R)$_2$), O, S, S(=O), S(=O)$_2$, N(R), P(R), and P(=O)(R); and $R_3$ is selected from any of H and methyl, and R is selected from any of H, methyl, aryl or heteroaryl.

5. The organic light-emitting device according to claim 4, wherein the material of the electron transport layer is selected from any one or a combination of two or more of following compounds:

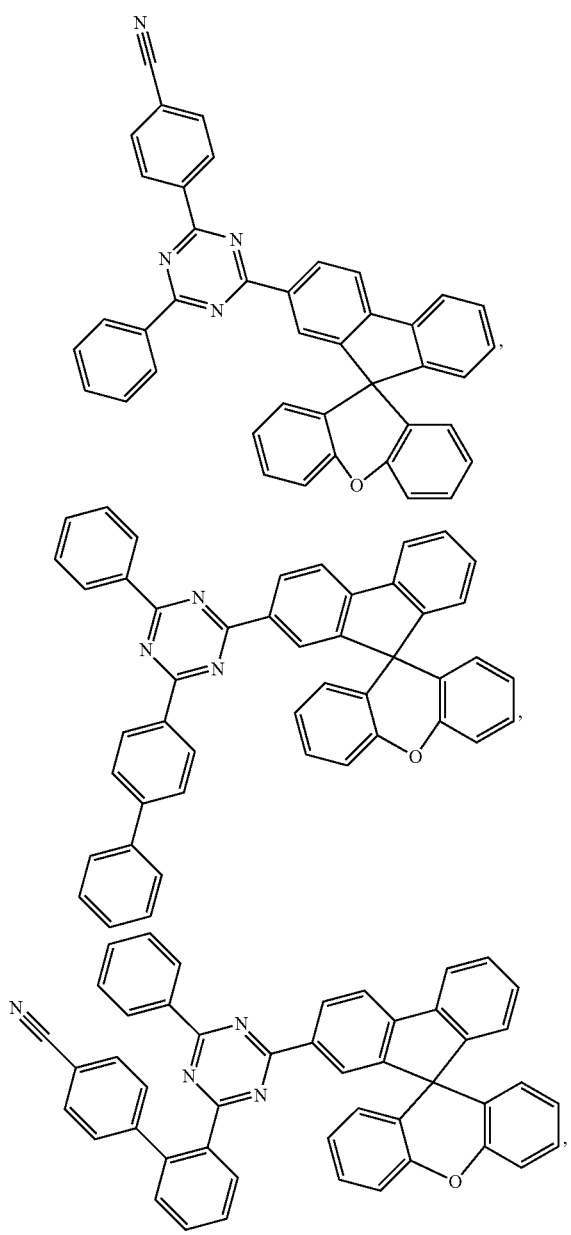

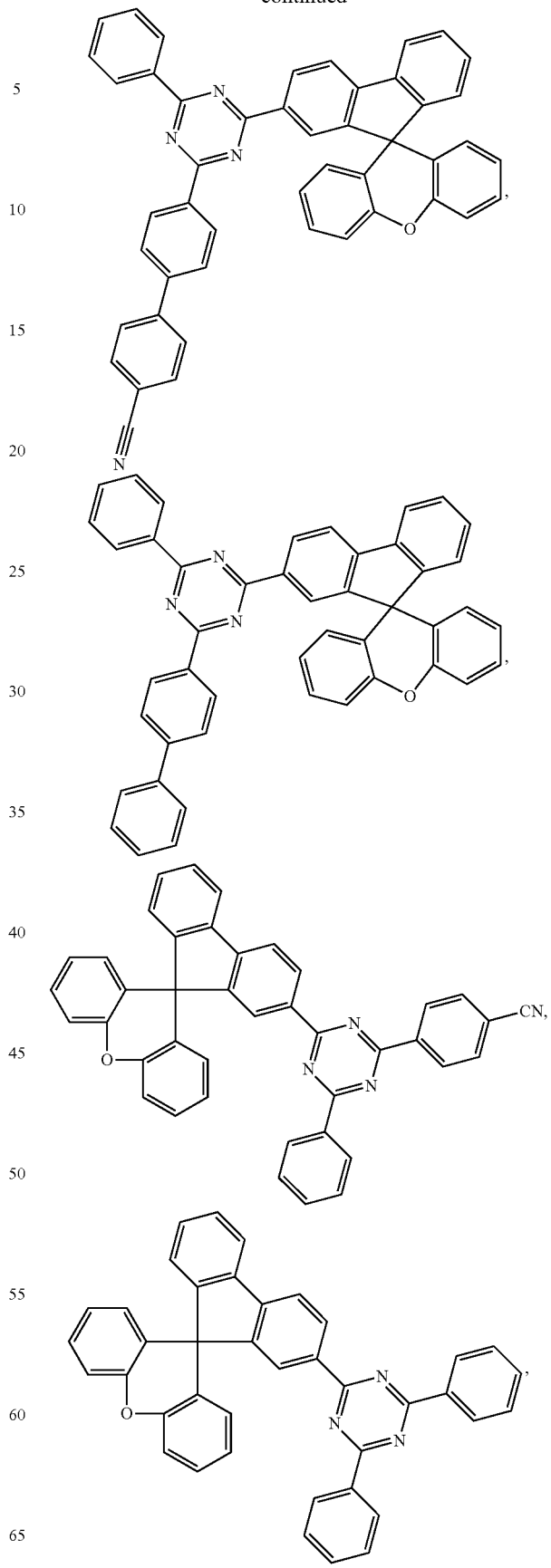

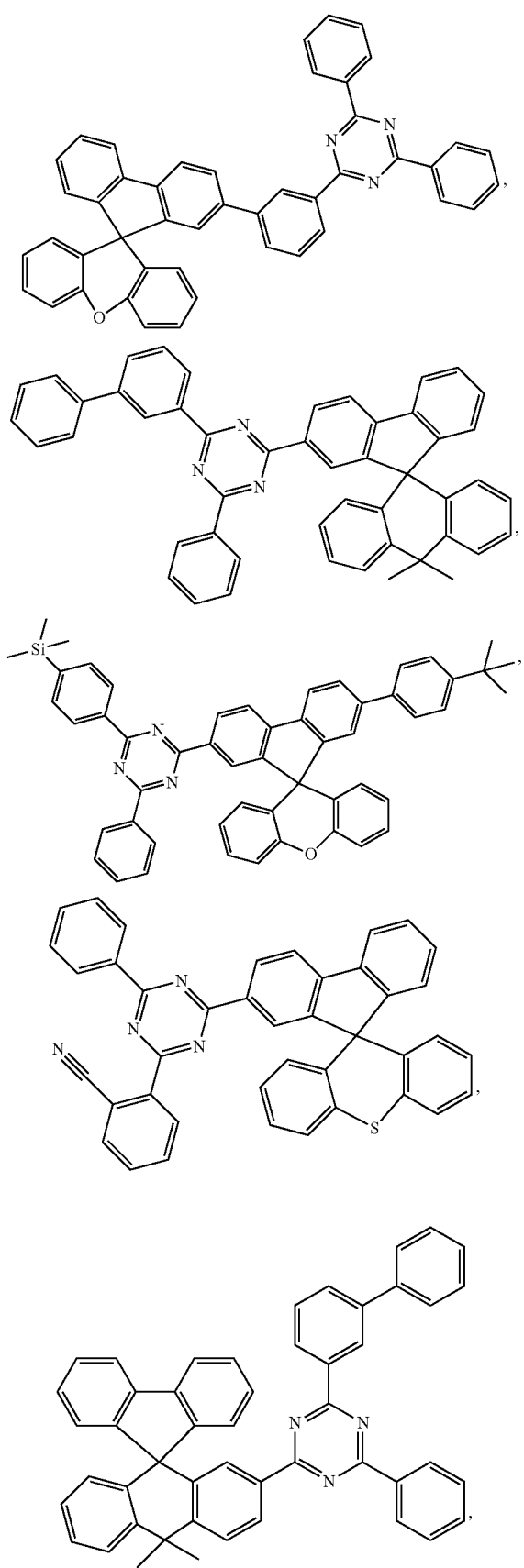
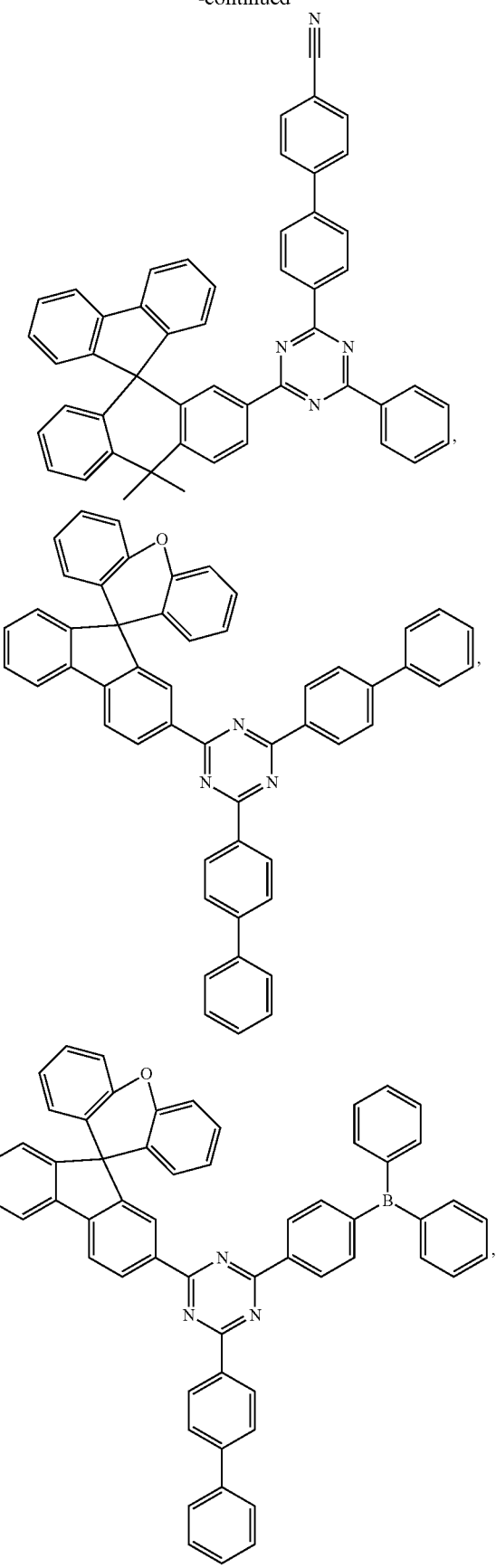

-continued

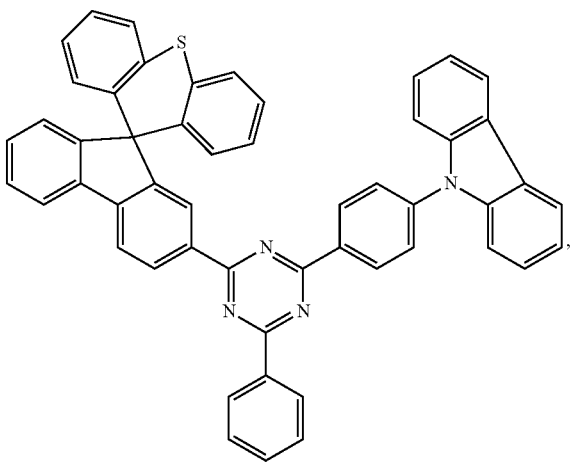

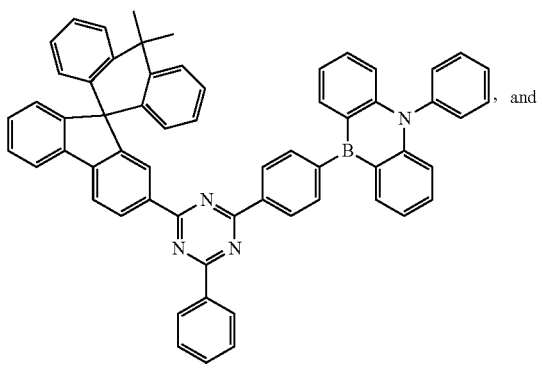

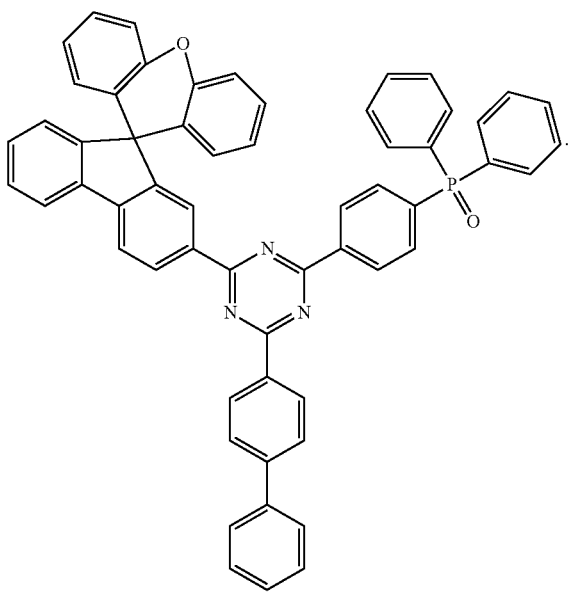

6. The organic light-emitting device according to claim 1, wherein the material of the hole blocking layer is selected from any one or a combination of two or more of structures as shown in a general formula (III):

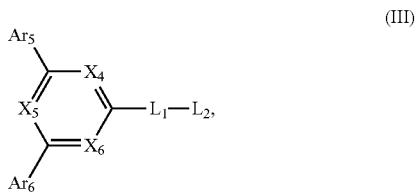

(III)

in the general formula (III), $X_4$, $X_5$, and $X_6$ are each independently selected from any of C(R) and N, and at least two of $X_4$, $X_5$, and $X_6$ are selected from N; and $Ar_5$, $Ar_6$, and $L_2$ are each independently selected from aryl with 6 to 60 carbon atoms substituted or unsubstituted by a substituent $R_1$, or heteroaryl with 2 to 60 carbon atoms substituted or unsubstituted by the substituent $R_1$;

$L_1$ is selected from a single bond, divalent aryl with 6 to 60 carbon atoms substituted or unsubstituted by the substituent $R_1$, or divalent heteroaryl with 2 to 60 carbon atoms substituted or unsubstituted by the substituent $R_1$;

$R_1$ is independently selected from any of tert-butyl, cyano, aryl or heteroaryl with 5 to 30 ring atoms, and —$Y_1$(Ar)$_n$, $Y_1$ is selected from carbon, nitrogen, phosphorus, silicon, boron, C(R$_3$)$_2$, Si(R$_3$)$_2$, C(=O), C(=NR), C(=C(R)$_2$), S(=O), S(=O)$_2$, and P(=O), n is an integer greater than or equal to 1, each Ar is the same or different, and is independently selected from aryl or heteroaryl, or Ar and the aryl or heteroaryl substituted by the substituent $R_1$ are connected as a ring through a single bond or a second bridging group, and/or at least two Ars, in a case where n is an integer greater than or equal to 2, are connected as a ring through a single bond or a second bridging group, and each second bridging group is selected from B(R), C(R)$_2$, Si(R)$_2$, C(=O), C(=NR), C(=C(R)$_2$), O, S, S (=O), S(=O)$_2$, N(R), P(R), and P(=O)(R); and $R_3$ is selected from any of H and methyl, and R is selected from any of H, methyl, aryl, and heteroaryl.

7. The organic light-emitting device according to claim 6, wherein in the general formula (III), in a case where $L_1$ is selected from divalent bicyclic aryl substituted or unsubstituted by the substituent $R_1$, at least one single ring in the divalent bicyclic aryl has a group attached at a meta position and/or an ortho position; and in a case where $L_1$ is selected from monocyclic aryl substituted or unsubstituted by the substituent $R_1$, $L_2$ and azine are attached at a meta position or an ortho position of $L_1$.

8. The organic light-emitting device according to claim 7, wherein the material of the hole blocking layer is selected from any one or a combination of two or more of following structures:

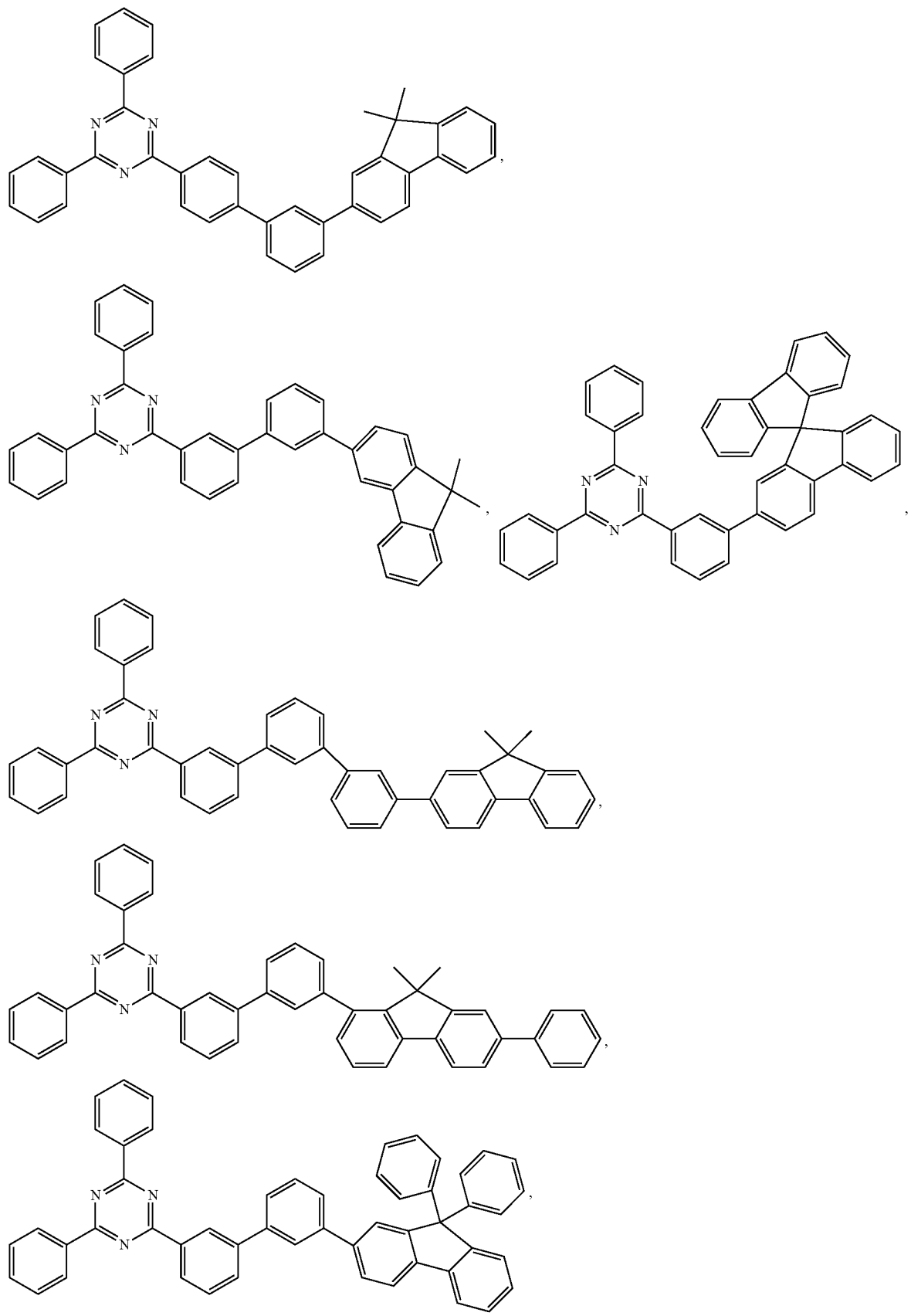

-continued

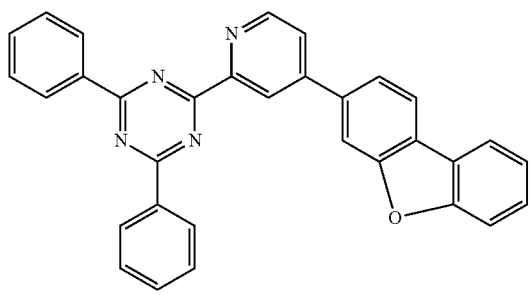
,

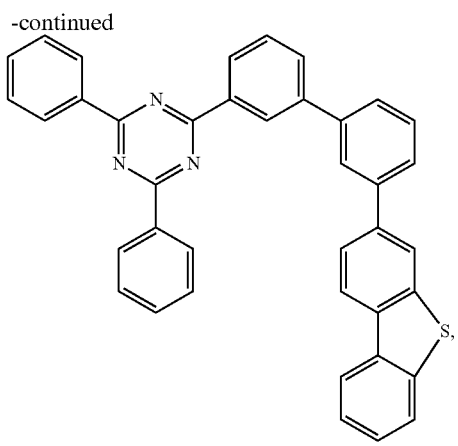
,

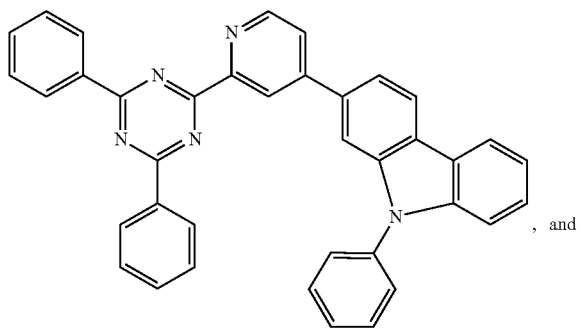
, and

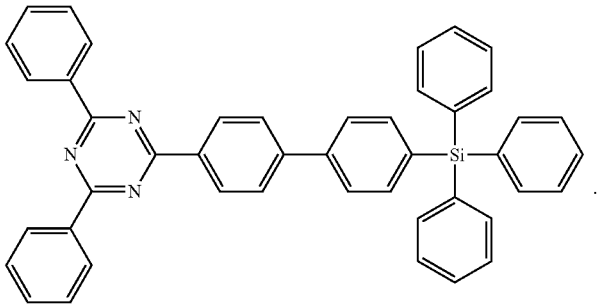
.

9. The organic light-emitting device according to claim 1, wherein
the first functional material layer includes a hole transport layer and an electron blocking layer; and
a hole mobility of a material of the hole transport layer is the same as a hole mobility of a material of the electron blocking layer; or
under a same test condition, the hole mobility of the material of the electron blocking layer is not less than one tenth of the hole mobility of the material of the hole transport layer.

10. The organic light-emitting device according to claim 9, wherein
a difference between a highest occupied molecular orbital (HOMO) energy level of the material of the hole transport layer and a HOMO energy level of the material of the electron blocking layer is greater than or equal to −0.5 eV, and is less than or equal to 0.3 eV.

11. The organic light-emitting device according to claim 9, wherein
a lowest triplet energy of the hole transport layer is greater than a lowest triplet energy of the electron blocking layer.

12. The organic light-emitting device according to claim 1, wherein
a material of the emitting layer includes a host material, and a difference between a highest occupied molecular orbital (HOMO) energy level of the hole blocking layer and a HOMO energy level of the host material is greater than or equal to 0.1 eV.

13. The organic light-emitting device according to claim 12, wherein
a lowest triplet energy of the hole blocking layer is greater than a lowest triplet energy of the host material.

14. The organic light-emitting device according to claim 12, wherein
the first functional material layer includes an electron blocking layer, and a difference between the HOMO energy level of the host material and a HOMO energy level of the electron blocking layer is less than or equal to 0.3 eV.

15. The organic light-emitting device according to claim 14, wherein
a lowest triplet energy of the electron blocking layer is greater than a lowest triplet energy of the host material.

16. The organic light-emitting device according to claim 9, wherein
the material of the hole transport layer and the material of the electron blocking layer are each independently selected from any of aromatic amine compounds.

17. A light-emitting substrate, comprising:
a base; and
a plurality of light-emitting devices disposed on the base; and
at least one light-emitting device being selected from the organic light-emitting device according to claim 1.

18. A light-emitting apparatus, comprising the light-emitting substrate according to claim 17.

19. An organic light-emitting device, comprising:
an anode, an emitting layer and a cathode that are stacked;
a first functional material layer located between the emitting layer and the anode; and
a second functional material layer located between the emitting layer and the cathode; and
under a same test condition, a hole mobility of a material of the first functional material layer being at least ten times an electron mobility of a material of the second functional material layer;

wherein the second functional material layer includes an electron transport layer and a hole blocking layer;

an electron mobility of a material of the electron transport layer is the same as an electron mobility of a material of the hole blocking layer; or, under a same test condition, the electron mobility of the material of the hole blocking layer is less than the electron mobility of the material of the electron transport layer; and a lowest triplet energy of the material of the electron transport layer is greater than a lowest triplet energy of the material of the hole blocking layer.

20. An organic light-emitting device, comprising:

an anode, an emitting layer and a cathode that are stacked;

a first functional material layer located between the emitting layer and the anode; and a second functional material layer located between the emitting layer and the cathode; and under a same test condition, a hole mobility of a material of the first functional material layer being at least ten times an electron mobility of a material of the second functional material layer;

wherein the first functional material layer includes a hole transport layer and an electron blocking layer;

a hole mobility of a material of the hole transport layer is the same as a hole mobility of a material of the electron blocking layer; or, under a same test condition, the hole mobility of the material of the electron blocking layer is not less than one tenth of the hole mobility of the material of the hole transport layer; and a lowest triplet energy of the hole transport layer is greater than a lowest triplet energy of the electron blocking layer.

* * * * *

UNITED STATES PATENT AND TRADEMARK OFFICE
CERTIFICATE OF CORRECTION

PATENT NO.        : 12,396,319 B2  
APPLICATION NO.   : 17/626147  
DATED             : August 19, 2025  
INVENTOR(S)       : Rongrong Gao and Lei Chen Page 1 of 1

It is certified that error appears in the above-identified patent and that said Letters Patent is hereby corrected as shown below:

In the Claims

Columns 45-46, Lines 20-65, (Claim 5): should be deleted and replaced with the following:

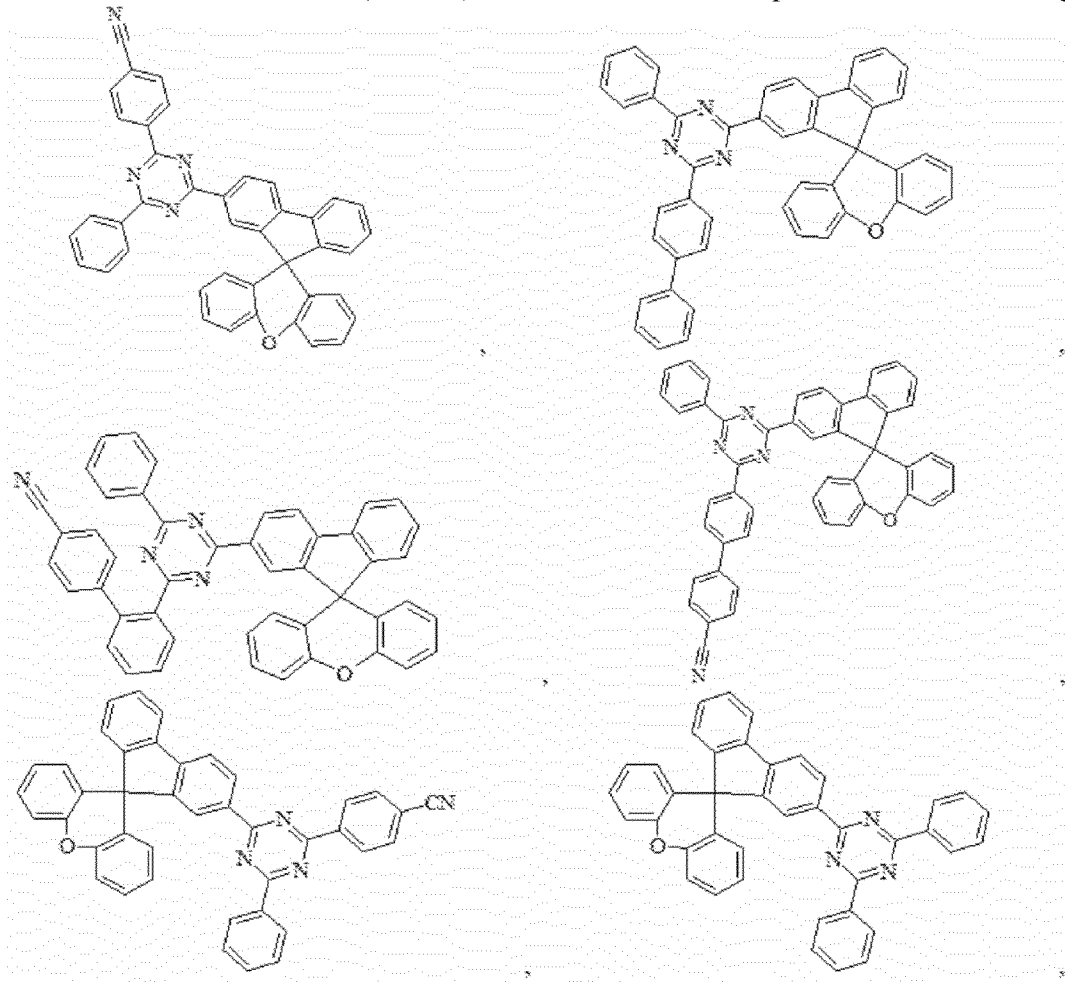

Signed and Sealed this  
Twenty-fifth Day of November, 2025

John A. Squires  
*Director of the United States Patent and Trademark Office*